United States Patent
Jacobs et al.

(10) Patent No.: US 9,452,135 B2
(45) Date of Patent: Sep. 27, 2016

(54) GELLING AGENT-BASED DOSAGE FORM

(71) Applicant: PARTICLE DYNAMICS INTERNATIONAL, LLC, St. Louis, MO (US)

(72) Inventors: Irwin Jacobs, St. Louis, MO (US); Stephen Gee, St. Louis, MO (US); Paul Brady, St. Louis, MO (US)

(73) Assignee: Particle Dynamics International, LLC, St. Louis, MO (US)

( * ) Notice: Subject to any disclaimer, the term of this patent is extended or adjusted under 35 U.S.C. 154(b) by 0 days.

(21) Appl. No.: 14/383,163

(22) PCT Filed: Mar. 19, 2013

(86) PCT No.: PCT/US2013/032946
§ 371 (c)(1),
(2) Date: Sep. 5, 2014

(87) PCT Pub. No.: WO2013/142482
PCT Pub. Date: Sep. 26, 2013

(65) Prior Publication Data
US 2015/0140113 A1    May 21, 2015

Related U.S. Application Data

(60) Provisional application No. 61/791,967, filed on Mar. 15, 2013, provisional application No. 61/613,119, filed on Mar. 20, 2012.

(51) Int. Cl.
| | |
|---|---|
| *A61K 9/107* | (2006.01) |
| *A61K 31/137* | (2006.01) |
| *A61K 31/167* | (2006.01) |
| *A61K 31/197* | (2006.01) |
| *A61K 31/455* | (2006.01) |
| *A61K 35/60* | (2006.01) |
| *A61K 47/02* | (2006.01) |
| *A61K 47/12* | (2006.01) |
| *A61K 47/14* | (2006.01) |
| *A61K 47/26* | (2006.01) |

(Continued)

(52) U.S. Cl.
CPC .................. *A61K 9/107* (2013.01); *A23L 1/05* (2013.01); *A23L 1/052* (2013.01); *A23L 1/054* (2013.01); *A23L 1/0526* (2013.01); *A23L 1/0545* (2013.01); *A23L 1/3008* (2013.01); *A61K 9/0065* (2013.01); *A61K 9/06* (2013.01); *A61K 9/146* (2013.01); *A61K 9/148* (2013.01); *A61K 9/7007* (2013.01); *A61K 31/137* (2013.01); *A61K 31/167* (2013.01); *A61K 31/192* (2013.01); *A61K 31/197* (2013.01); *A61K 31/455* (2013.01); *A61K 35/60* (2013.01); *A61K 45/06* (2013.01); *A61K 47/02* (2013.01); *A61K 47/12* (2013.01); *A61K 47/14* (2013.01); *A61K 47/26* (2013.01); *A61K 47/36* (2013.01); *A61K 47/46* (2013.01); *A23V 2002/00* (2013.01)

(58) Field of Classification Search
CPC .... A61K 45/06; A61K 31/192; A61K 47/12; A61K 47/14; A61K 47/26; A61K 47/46; A61K 31/197; A61K 9/0065; A61K 9/06; A61K 47/36; A61K 9/146; A61K 9/148; A61K 9/7007; A61K 31/137; A61K 31/167; A61K 9/107; A61K 47/02; A61K 35/60; A61K 31/455; A23L 1/3008; A23L 1/05; A23L 1/0526; A23L 1/054; A23V 2002/00; A23V 2200/30; A23V 2200/31; A23V 2200/326; A23V 2250/186; A23V 2250/1882
See application file for complete search history.

(56) References Cited

U.S. PATENT DOCUMENTS

| | | | |
|---|---|---|---|
| 4,140,755 | A | 2/1979 | Sheth et al. |
| 4,307,124 | A | 12/1981 | Moirano |

(Continued)

FOREIGN PATENT DOCUMENTS

| | | |
|---|---|---|
| EP | 0873749 B1 | 3/2006 |
| JP | 56097220 A | 8/1981 |

(Continued)

OTHER PUBLICATIONS

International Search Report, PCT/US2013/032946, dated Sep. 10, 2013, 8 pages.

(Continued)

*Primary Examiner* — Anoop Singh
*Assistant Examiner* — Doan Phan
(74) *Attorney, Agent, or Firm* — Senniger Powers LLP

(57) ABSTRACT

The present invention generally relates to dosage forms for oral administration including one or more gelling agents. In particular, the present invention is directed to gelling agent-based dosage forms that are easily administered and taken, or swallowed. The present invention is also directed to gelling agent-based dosage forms that exhibit relatively low syneresis, are thermally stable, exhibit substantially constant active ingredient concentration, and/or exhibit one or more advantageous rheological properties. In particular, the present invention is directed to such gels containing one or more omega-3 fatty acids. The gelling agent-based dosage forms of the present invention are suitable for administration of a relatively large dose of active ingredient. The gelling agent-based dosage forms of the present invention are also suitable for administration of multiple active ingredients. Dosage forms of the present invention also provide tamper resistance and, thus, prevent recovery or diversion of active ingredients contained therein. The gelling agent-based dosage forms are also suitable for use as gastro-retentive and sustained release dosage forms.

18 Claims, 9 Drawing Sheets

(51) Int. Cl.
*A61K 47/36* (2006.01)
*A61K 47/46* (2006.01)
*A61K 9/00* (2006.01)
*A61K 9/06* (2006.01)
*A61K 9/14* (2006.01)
*A61K 9/70* (2006.01)
*A61K 31/192* (2006.01)
*A61K 45/06* (2006.01)
*A23L 1/30* (2006.01)
*A23L 1/05* (2006.01)
*A23L 1/052* (2006.01)
*A23L 1/0526* (2006.01)
*A23L 1/054* (2006.01)

(56) References Cited

U.S. PATENT DOCUMENTS

| | | |
|---|---|---|
| 4,414,236 A * | 11/1983 | Moran et al. ............ 426/573 |
| 4,451,260 A | 5/1984 | Mitra |
| 4,525,306 A | 6/1985 | Yajima |
| 4,610,870 A | 9/1986 | Jain et al. |
| 4,647,470 A | 3/1987 | Sanderson et al. |
| 4,655,840 A | 4/1987 | Wittwer et al. |
| 4,676,976 A | 6/1987 | Toba et al. |
| 4,746,528 A | 5/1988 | Prest et al. |
| 4,780,320 A | 10/1988 | Baker |
| 4,788,220 A | 11/1988 | Mody et al. |
| 4,814,179 A | 3/1989 | Bolton et al. |
| 4,975,465 A | 12/1990 | Motola et al. |
| 4,994,276 A | 2/1991 | Baichwal et al. |
| 5,002,934 A | 3/1991 | Norton et al. |
| 5,051,262 A | 9/1991 | Panoz et al. |
| 5,084,278 A | 1/1992 | Mehta |
| 5,128,143 A | 7/1992 | Baichwal et al. |
| 5,210,099 A | 5/1993 | Mody et al. |
| 5,232,704 A | 8/1993 | Franz et al. |
| 5,240,996 A | 8/1993 | D'Amelia et al. |
| 5,288,479 A | 2/1994 | Gorman et al. |
| 5,288,500 A | 2/1994 | Ibsen |
| 5,342,626 A | 8/1994 | Winston, Jr. et al. |
| 5,360,793 A | 11/1994 | Brooks |
| 5,385,747 A | 1/1995 | Katz et al. |
| 5,399,359 A | 3/1995 | Baichwal |
| 5,422,134 A | 6/1995 | Hart et al. |
| 5,434,183 A | 7/1995 | Larsson-Backstrom |
| 5,455,046 A | 10/1995 | Baichwal |
| 5,498,436 A | 3/1996 | Modliszewski et al. |
| 5,525,351 A | 6/1996 | Dam |
| 5,532,002 A | 7/1996 | Story |
| 5,552,462 A | 9/1996 | Yeh |
| 5,576,039 A | 11/1996 | Lewis |
| 5,624,612 A | 4/1997 | Sewall et al. |
| 5,645,856 A | 7/1997 | Lacy et al. |
| 5,730,997 A | 3/1998 | Lienhop et al. |
| 5,773,025 A | 6/1998 | Baichwal |
| 5,811,148 A | 9/1998 | Chiu et al. |
| 5,846,563 A | 12/1998 | Baichwal |
| 5,932,235 A | 8/1999 | Ninomiya et al. |
| 6,018,935 A | 2/2000 | Perrone |
| 6,063,915 A | 5/2000 | Hansen et al. |
| 6,099,876 A | 8/2000 | Nussinovitch |
| 6,102,254 A | 8/2000 | Ross |
| 6,136,343 A | 10/2000 | Baichwal |
| 6,183,801 B1 | 2/2001 | Warendorf |
| 6,245,356 B1 | 6/2001 | Baichwal |
| 6,337,083 B1 | 1/2002 | Fuisz |
| 6,485,771 B1 | 11/2002 | Somerville et al. |
| 6,500,459 B1 | 12/2002 | Chhabra et al. |
| 6,521,257 B1 | 2/2003 | Taniguchi et al. |
| 6,572,898 B2 | 6/2003 | Nelson et al. |
| 6,586,590 B1 | 7/2003 | Renn et al. |
| 6,592,863 B2 | 7/2003 | Fuchs et al. |
| 6,592,926 B2 | 7/2003 | Ong et al. |
| 6,610,667 B1 | 8/2003 | Dettmar et al. |
| 6,656,482 B2 | 12/2003 | Mehta et al. |
| 6,669,954 B2 | 12/2003 | Crison et al. |
| 6,689,812 B2 | 2/2004 | Peet et al. |
| 6,723,340 B2 | 4/2004 | Gusler et al. |
| 6,726,928 B2 | 4/2004 | Yarwood et al. |
| 6,887,850 B2 | 5/2005 | Fuchs et al. |
| 7,037,570 B2 | 5/2006 | Ueda et al. |
| 7,157,100 B2 | 1/2007 | Doshi et al. |
| 7,208,480 B2 | 4/2007 | Williams et al. |
| 7,211,283 B2 | 5/2007 | Jones et al. |
| 7,338,679 B2 | 3/2008 | Uchida et al. |
| 7,442,541 B2 | 10/2008 | Tsubaki et al. |
| 7,531,192 B2 | 5/2009 | Farber et al. |
| 7,560,486 B2 | 7/2009 | Carpentier et al. |
| 7,652,068 B2 | 1/2010 | Feuerstein et al. |
| 7,713,551 B2 | 5/2010 | McGurk et al. |
| 8,003,152 B1 | 8/2011 | Xiong et al. |
| 8,071,646 B2 | 12/2011 | Feuerstein et al. |
| 2003/0165604 A1 | 9/2003 | Tsubaki et al. |
| 2004/0018248 A1 | 1/2004 | Bendich |
| 2004/0043043 A1 * | 3/2004 | Schlyter et al. ............ 424/400 |
| 2004/0057981 A1 | 3/2004 | Base et al. |
| 2004/0091528 A1 | 5/2004 | Rogers et al. |
| 2004/0121012 A1 | 6/2004 | Baichwal |
| 2004/0131645 A1 | 7/2004 | Williams et al. |
| 2004/0137040 A1 | 7/2004 | Nogami |
| 2004/0248974 A1 | 12/2004 | Holmberg |
| 2005/0118254 A1 | 6/2005 | Choi et al. |
| 2005/0147665 A1 | 7/2005 | Horrobin et al. |
| 2006/0004099 A1 | 1/2006 | Roe |
| 2006/0034815 A1 | 2/2006 | Guzman et al. |
| 2006/0251768 A1 | 11/2006 | Bouquerand |
| 2006/0286184 A1 | 12/2006 | Nativ et al. |
| 2007/0128142 A1 | 6/2007 | Harrison et al. |
| 2007/0128285 A1 | 6/2007 | Jin et al. |
| 2007/0131342 A1 | 6/2007 | Buhrow et al. |
| 2007/0141152 A1 | 6/2007 | Nogami |
| 2007/0213234 A1 | 9/2007 | Yaghmur et al. |
| 2007/0218137 A1 | 9/2007 | Baichwal et al. |
| 2007/0259957 A1 * | 11/2007 | Ueshima et al. ............ 514/546 |
| 2008/0107789 A1 | 5/2008 | Akimoto |
| 2008/0146472 A1 | 6/2008 | Brooks |
| 2008/0160087 A1 | 7/2008 | Ishibashi et al. |
| 2008/0255247 A1 | 10/2008 | Sagalowicz et al. |
| 2008/0261896 A1 | 10/2008 | Tanaka et al. |
| 2008/0299199 A1 | 12/2008 | Bar-Shalom et al. |
| 2009/0011012 A1 | 1/2009 | Baum |
| 2009/0011048 A1 | 1/2009 | Coleman et al. |
| 2009/0030077 A1 | 1/2009 | Almarsson et al. |
| 2009/0074940 A1 | 3/2009 | Sliwinski |
| 2009/0137556 A1 | 5/2009 | Bonnichsen |
| 2009/0169498 A1 | 7/2009 | de Jong |
| 2009/0252792 A1 | 10/2009 | Verbruggen et al. |
| 2009/0285869 A1 | 11/2009 | Trimble |
| 2010/0130608 A1 | 5/2010 | Ryan et al. |
| 2010/0160435 A1 | 6/2010 | Bruzzese |
| 2011/0027412 A1 | 2/2011 | Spence et al. |
| 2011/0044964 A1 | 2/2011 | Davis |
| 2011/0111108 A1 | 5/2011 | Craig et al. |
| 2011/0177176 A1 | 7/2011 | Sridhar |
| 2011/0262534 A1 | 10/2011 | Berge et al. |
| 2011/0268770 A1 | 11/2011 | Seternes et al. |
| 2011/0268771 A1 | 11/2011 | Seternes et al. |
| 2012/0225945 A1 | 9/2012 | Hustvedt et al. |
| 2012/0232141 A1 | 9/2012 | Hustvedt et al. |
| 2014/0242166 A1 | 8/2014 | Baichwal et al. |

FOREIGN PATENT DOCUMENTS

| | | |
|---|---|---|
| JP | 07138148 A | 5/1995 |
| JP | 2004089160 A | 3/2004 |
| JP | 2004099558 A1 | 4/2004 |
| WO | 9725024 A1 | 7/1997 |
| WO | 9801117 A1 | 1/1998 |

(56) References Cited

FOREIGN PATENT DOCUMENTS

| WO | 2004056370 A1 | 7/2004 |
|---|---|---|
| WO | 2007060177 A1 | 5/2007 |
| WO | 2007085840 A1 | 8/2007 |

OTHER PUBLICATIONS

Written Opinion, PCT1US20131032946, dated Sep. 10, 2013, 16 pages.
Abstract of JP56097220; Aug. 5, 1981.
Satyanarayana et al., "Gels and Jellies as a Dosage Form for Dysphagia Patients: A Review", Current Drug Therapy, 2011, vol. 6, pp. 79-86.
Gosh et al., Drug Development and Industrial Pharmacy, 1998, vol. 24, No. 5, pp. 473-477.
Ismail Mahmoud Khalifeh, "Thermodynamic evaluation of ibuprofen solubility in aqueous and non-aqueous cosolvent systems", Dec. 2000, A Thesis submitted to the faculty of Purdue University.
Rustan et al., "Fatty Acids: Structures and Properties", John Wiley & Sons, Ltd., Sep. 2005.
Welch et al., "Dietary intake and status of n-3 polyunsaturated fatty acids in a population of fish-eating and non-fisheating meat-eaters, vegetarians, and vegans and the precursor-product ratio of α-linolenic acid to long-chain n-3 polyunsaturated fatty acids: results from the EPIC-Norfolk cohort", Am J Clin Nutr, 2010, 92, pp. 1040-1051.
Uson et al., "Formation of water-in-oil (W/O) nano-emulsions in a water/mixed non-ionic surfactant/oil systems prepared by a low-energy emulsification method", Colloids and Surfaces a Physicochemical and Engineering Aspects 250 (1-3), 2004, pp. 415-421.
Written Opinion, PCT/US2013/032946, dated Apr. 7, 2014, 17 pages.

\* cited by examiner

Table Concentration of standards with their respective absorbance readings.
Figure Niacin standard curve. $\varepsilon = 4690.49\ M^{-1}\ cm^{-1}$ Graph 1: Stress-Strain Curve for 3 different gel samples.
① 61011-B
② 61411-A
③ 61011-A
Rupture Point: The maximum Stress over Strain value before breakage.
Gel Strength: The maximum Stress value before breakage.
Gel Extensibility: The maximum strain before breakage.

Kappa-carrageenan/xanthan gum/locust bean gum

Graph 1: Stress-Strain Curve for 3 different gel samples.
① 61011-B
② 61411-A
③ 61011-A
Modulus: The slope of the linear section at the very beginning of the stress-strain curve.

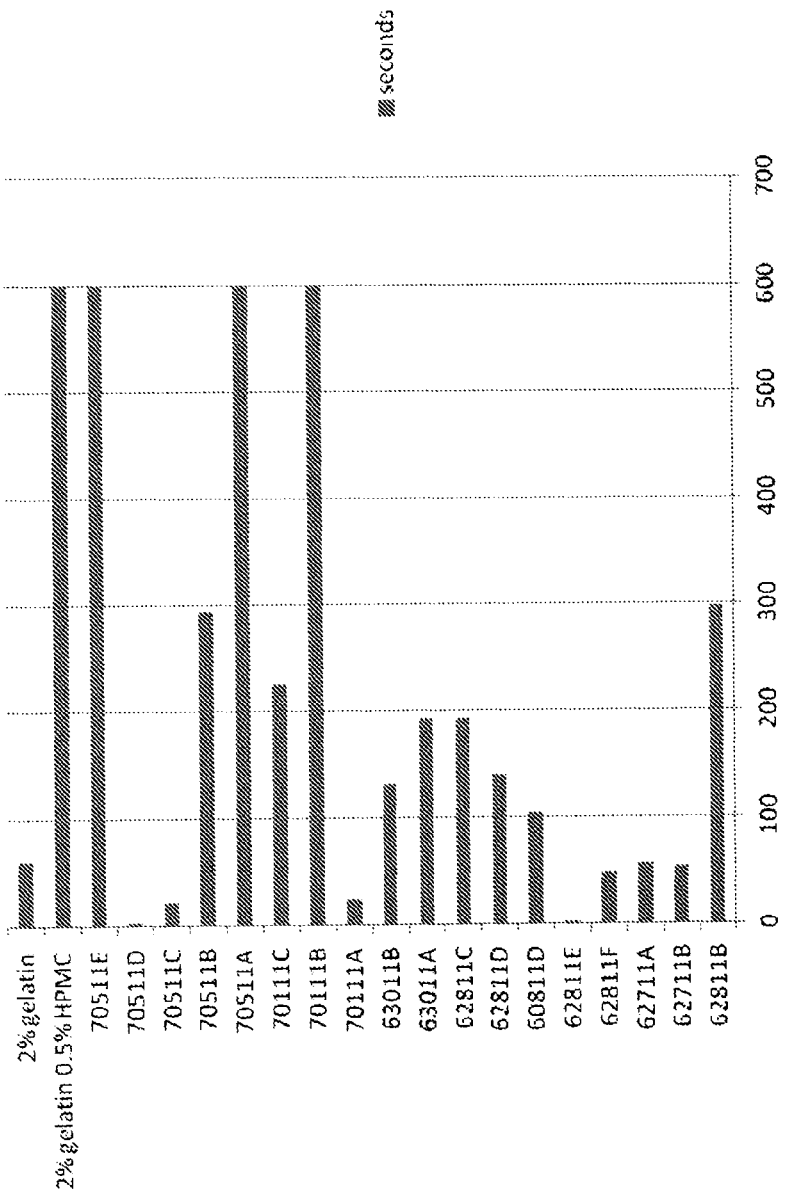

GELLING AGENT-BASED DOSAGE FORM

This application is a U.S. national stage application of International Patent Application No. PCT/US2013/032946, filed Mar. 19, 2013, and claims the benefit of U.S. Provisional Application No. 61/791,967, filed Mar. 15, 2013, and U.S. Provisional Application No. 61/613,119, filed Mar. 20, 2012, the entire disclosures of which are incorporated herein by reference.

FIELD OF THE INVENTION

The present invention generally relates to dosage forms and drug delivery systems for oral administration including one or more gelling agents. In particular, the present invention is directed to gelling agent-based dosage forms that are easily administered and taken, or swallowed. The present invention is also directed to gelling agent-based dosage forms that exhibit relatively low syneresis, are thermally stable, exhibit substantially constant active ingredient concentration, and/or exhibit one or more advantageous rheological properties. In particular, the present invention is directed to such gels containing one or more omega-3 fatty acids. The gelling agent-based dosage forms of the present invention are suitable for administration of a relatively large dose of active ingredient. The gelling agent-based dosage forms of the present invention are also suitable for administration of multiple active ingredients. Dosage forms of the present invention also provide tamper resistance and, thus, prevent recovery or diversion of active ingredients contained therein. The gelling agent-based dosage forms are also suitable for use as gastro-retentive and sustained release dosage forms.

BACKGROUND OF THE INVENTION

Inconvenience of administration and patient compliance are often significant concerns in connection with designing dosage forms for a variety of populations, including the elderly, children, and patients undergoing various treatments including, for example, chemotherapy. Difficulty swallowing, or dysphagia, is common among all patient populations, but often more prominent in the above-noted groups. For example, a high percentage of patients suffering from type-2 diabetes are elderly patients suffering from severe dysphagia. Subjects suffering from dysphagia may be choked or have a fear of being choked when taking a variety of dosage forms, including tablets, capsules, and viscous liquids. In view of the above, and various other considerations, many patients refuse to take required dosages or may require breakage of the dosage form. In addition to missing doses, breakage of dosage forms is undesired for a variety of reasons, including that the patient may not receive the required or recommended dose. Regardless of dysphagia or any fear of taking dosage forms or a fear of being choked, dosage forms that are more easily administered are desired for any patient or subject. For example, due to their ease in handling, the compositions of the present invention may be consumed as "on-the-go" by consumers while performing other activities. The visual and textural properties of the compositions of the present also make the compositions appealing to consumers, and particularly children. For example, the compositions of the present invention can be molded into a variety of shapes and/or a variety of colors may be incorporated that are appealing to children.

Dosage forms including one or more gelling agents are known in the art. However, many of these dosage forms suffer from one or more disadvantages. One disadvantage is formation of free water (i.e., un-gelled water) during storage, which is commonly referred to as syneresis. Formation of free, un-gelled water is undesired as it results in a change in the concentration of active ingredient and may also make the dosage form difficult to handle. Another disadvantage of many gelling agent-based dosage forms is thermal stability during storage. Many gelling agent-based dosage forms lose structural integrity during storage. In addition, certain gelling agent-based dosage forms may be difficult to consume (e.g., require significant chewing effort or pose a choking hazard) due to their insufficiently deformable structure provided by their gel strength.

For at least the foregoing reasons, there exists a need in the art for alternative gelling agent-based dosage forms that are more easily administered or taken and that also overcome one or more of the above-noted disadvantages associated with conventional gelling agent-based dosage forms.

SUMMARY OF THE INVENTION

Briefly, therefore, the present invention is directed to gelling agent-based dosage forms. The gelling agent-based dosage forms are easily administered and/or swallowed by any subject, regardless of the patient suffering from, for example, dysphagia or a fear of taking oral dosage forms. The dosage form of the present invention may exhibit the mouthfeel of a liquid soon after introduction into the mouth and/or after initiation of chewing by the patient. In this manner, the dosage form of the present invention may be referred to as a "chewable liquid." However, reference to a "chewable liquid" herein is not intended to refer to a "liquid" in the typical sense. In certain embodiments, the present invention is directed to omega-3 fatty acid-containing gels. The present invention is further directed to gelling agent-based dosage forms that are tamper-resistant, sustained release and/or gastro-retentive dosage forms. Tamper resistant dosage forms are those that prevent extraction of active ingredient and thus render diversion of the active ingredient for illegal uses or for delivery systems other than the intended oral route impossible, or nearly impossible. Sustained release systems provide release of the active ingredient over an extended period of time (e.g., over the course of from 8 to 12 hours) as compared to immediate release of traditional oral tablet dosage forms. Gastro-retentive dosage forms are those systems that are retained in the stomach by virtue of their size such that they can not move through the pyloric valve that controls stomach emptying or by their floating on stomach contents.

In various embodiments, the present invention is directed to an aqueous gel composition comprising an active ingredient; one or more gelling agents selected from the group consisting of xanthan gum, locust bean gum, gellan gum, guar gum, pullulan, konjac flour, kappa-carrageenan, iota-carrageenan, gum tragacanth, and combinations thereof; and water. In accordance with various such embodiments, water constitutes at least about 40 wt % of the composition, and (i) the Young's modulus of the composition (Pa/% strain) is from about 10 to about 95; and/or (ii) the Young's modulus of the composition (Pa/% strain) per unit composition surface area is from about 0.25 Pa/cm$^2$ to about 2.5 Pa/cm$^2$; and/or (iii) the active ingredient content varies by less than about 10% during storage of the composition under ambient conditions for 90 days; and/or (iv) syneresis of the composition during storage under ambient conditions for 90 days is less than about 10%; and/or (v) the active ingredient constitutes at least about 0.05 g per g composition.

In various other embodiments, the present invention is directed to an aqueous acetaminophen gel composition comprising acetaminophen or a pharmaceutically acceptable salt or derivative thereof; one or more gelling agents selected from the group consisting of xanthan gum, locust bean gum, gellan gum, guar gum, pullulan, konjac flour, kappa-carrageenan, iota-carrageenan, gum tragacanth, and combinations thereof; and water, wherein water constitutes at least about 40 wt % of the composition.

In still further embodiments the present invention is directed to an aqueous gel composition comprising an active ingredient; one or more gelling agents selected from the group consisting of locust bean gum, iota-carrageenan, kappa-carrageenan, gellan gum, and combinations thereof; a rheology modifier selected from the group consisting of xanthan gum, locust bean gum, guar gum, methyl cellulose, and combinations thereof; a syneresis controlling agent selected from the group consisting of konjac flour, gum tragacanth, pullulan, gellan gum, and combinations thereof; and water.

In various other embodiments, the present invention is directed to an aqueous gel composition comprising an active ingredient; water; and one or more gelling agents selected from the group consisting of locust bean gum, iota-carrageenan, kappa-carrageenan, gellan gum, xanthan gum, konjac flour, gum tragacanth, pullulan, gellan gum, and combinations thereof. In accordance with such embodiments, (i) the composition exhibits a gel strength of from about 4 kPa to about 70 kPa at the gel rupture point; and/or (ii) the composition exhibits a gel strength of from about 0.1 to about 1.75 kPa/cm$^2$ surface area; (iii) the composition exhibits an extensibility of from about 50.0 to about 80.0%; and/or (iv) the composition exhibits an extensibility of from about 1 to about 2%/m$^2$ surface area; (v) when a force of from about 0.1 lbs to about 2.2 lbs is applied to the gel composition, the stress-strain curve of the gel composition exhibits a rupture point of from about 90 to about 1000 Pa/%, wherein the rupture point is defined as the ratio of the gel strength (Pa) and the extensibility (%) at the rupture point of the gel; and/or (vi) when the gel composition is stored under ambient conditions for up to about 90 days, the syneresis of the composition is less than about 5%; and/or (vii) when the gel composition is stored under ambient conditions for up to about 90 days, the total syneresis is no more than about 15 mg/cm$^2$ composition surface area; (viii) when the aqueous gel is in the form of a cylinder, the composition passes under the force of gravity through an un-lubricated cylinder having a length of 8 inches and an inner diameter substantially equal to the diameter of the cylindrical composition in less than about 500 seconds; and/or (ix) when the aqueous gel is in the form of a cylinder the composition passes through an un-lubricated cylinder having an inner diameter substantially equal to the diameter of the cylindrical composition at a rate of at least about 0.016 in/sec.

In still further embodiments, the present invention is directed to an aqueous gel composition comprising (i) an active ingredient; (ii) water; (iii) gellan gum in a proportion of from 0.1 to about 1 wt. % of the composition; (iv) locust bean gum in a proportion of from 0.1 to 1 wt. % of the composition; (v) xanthan gum in a proportion of from 0.1 to 1 wt. % of the composition; and (vi) a source of potassium ions, a source of sodium ions, or a combination thereof in a proportion of from about 0.05 to about 1 wt. % of the composition.

In various other embodiments, the present invention is directed to an aqueous gel composition comprising (i) an active ingredient; (ii) water; (iii) gellan gum; (iv) xanthan gum; and (v) locust bean gum, wherein locust bean gum constitutes from about 0.1 to about 1 wt. % of the composition and when the gel composition is stored under ambient conditions for up to about 90 days, syneresis is less than about 5%.

In further embodiments, the present invention is directed to an aqueous gel composition comprising (i) an active ingredient; (ii) water; (iii) carrageenan; (iv) xanthan gum; (v) locust bean gum; and (vi) a source of potassium ions, wherein the source of potassium ions constitutes from about 0.05 to about 1 wt. % of the composition.

In various other embodiments, the present invention is directed to an acid-free aqueous gel composition comprising (i) an active ingredient; (ii) water; (iii) carrageenan; (iv) xanthan gum; (v) locust bean gum; and (vi) a source of potassium ions.

In even further embodiments, the present invention is directed to an aqueous gel composition comprising (i) an active ingredient; (ii) water; (iii) konjac flour in a proportion of from 0.1 to about 1 wt. % of the composition; (iv) locust bean gum in a proportion of from 0.1 to 1 wt. % of the composition; and (v) xanthan gum in a proportion of from 0.1 to 1 wt. % of the composition.

In still further embodiments, the present invention is directed to an aqueous gel composition comprising (i) an active ingredient; (ii) water; (iii) pullulan in a proportion of from 0.1 to about 1 wt. % of the composition; (iv) locust bean gum in a proportion of from 0.1 to 1 wt. % of the composition; (v) xanthan gum in a proportion of from 0.1 to 1 wt. % of the composition; and (vi) a source of potassium ions, calcium ions, sodium ions, or a combination thereof in a proportion of at least about 0.05 wt % of the composition.

In various other embodiments, the present invention is directed to an aqueous gel composition comprising pseudoephedrine; water; and one or more gelling agents selected from the group consisting of locust bean gum, iota-carrageenan, kappa-carrageenan, gellan gum, xanthan gum, konjac flour, gum tragacanth, pullulan, gellan gum, and combinations thereof.

The present invention is also directed to oral dosage forms comprising a pharmaceutically active ingredient dispersed throughout a tamper-resistant gel composition. In accordance with such embodiments the gel composition comprises (i) one or more gelling agents selected from the group consisting of locust bean gum, iota-carrageenan, kappa-carrageenan, gellan gum, and combinations thereof; (ii) a rheology modifier selected from the group consisting of xanthan gum, locust bean gum, guar gum, methyl cellulose, and combinations thereof; and (iii) a syneresis controlling agent selected from the group consisting of konjac flour, gum tragacanth, pullulan, gellan gum, and combinations thereof.

In various other embodiments, the present invention is directed to a method for preventing the recovery of a pharmaceutically active ingredient from an oral dosage form. The method comprises (i) forming an aqueous composition comprising one or more gelling agents selected from the group consisting of locust bean gum, iota-carrageenan, kappa-carrageenan, gellan gum, xanthan gum, konjac flour, gum tragacanth, pullulan, gellan gum, and combinations thereof; (ii) dispersing the pharmaceutically active ingredient throughout the aqueous composition; and (iii) allowing the aqueous composition having the pharmaceutically active ingredient dispersed throughout to form an oral dosage form in the form an aqueous gel composition having the pharmaceutically active ingredient dispersed therein.

In still further embodiments, the present invention is directed to a gastro-retentive dosage form. The dosage form is in the form of an aqueous gel composition comprising (i) an active ingredient, (ii) water, (iii) a plurality of gelling agents selected from the group consisting of locust bean gum, iota-carrageenan, kappa-carrageenan, gellan gum, xanthan gum, konjac flour, pullulan, karaya, tragacanth, and combinations thereof, and (iv) an alkali metal carbonate or bicarbonate, wherein the gel composition is buoyant in an acidic liquid medium for at least about 24 hours.

In still further embodiments, the present invention is directed to a sustained release dosage form for oral administration. The dosage form is in the form of an aqueous gel composition comprising (i) water, (ii) an active ingredient, (iii) a plurality of gelling agents selected from the group consisting of locust bean gum, iota-carragenenan, kappa-carrageenan, gellan gum, xanthan gum, konjac flour, pullulan, karaya, tragacanth, and combinations thereof, and (iv) an alkali metal carbonate or bicarbonate. The gel composition delivers: (a) from about 90 to about 100% of the active ingredient in from about 0 to about 4 hours after administration, and/or (b) from about 60 to about 65% of the active ingredient in from about 0 to about 8 hours after administration, and/or (c) from about 65 to about 85% of the active ingredient in from about 0 to about 12 hours after administration, and/or (d) from about 85 to about 90% of the active ingredient in from about 0 to about 16 hours after administration, and/or (e) from 90 to 95% of an effective amount of the active ingredient in from about 0 to about 20 hours after administration, and/or (f) from 90 to 100% of an effective amount of the active ingredient in from about 0 to about 24 hours after administration.

In various embodiments, the present invention is directed to aqueous omega-3 fatty acid gel compositions, wherein water constitutes at least 30 wt % of the composition, and the composition is defined by at least one of the following features: a Young's modulus (Pa/% strain) of from about 10 to about 95; and/or a Young's modulus (Pa/% strain) per unit composition surface area of from about 0.25 Pa/cm2 to about 10 Pa/cm$^2$; and/or a gel strength per unit composition surface area is from about 0.1 to about 1.75 kPa/cm$^2$; and/or an extensibility of from about 50% to about 90%; and/or when a force of from about 0.1 lbs to about 2.2 lbs is applied to the gel composition, the stress-strain curve of the gel composition exhibits a rupture point of from about 90 to about 1000 Pa/%, wherein the rupture point is defined as the ratio of the gel strength (Pa) and the extensibility (%) at the rupture point of the gel; and/or the composition has an omega-3 fatty acid content of at least about 50 mg/g.

In still further embodiments, the present invention directed to an aqueous omega-3 fatty acid gel composition, the composition comprising water, one or more gelling, and one or more omega-3 fatty acids, wherein: (i) water constitutes at least 30 wt % of the composition; (ii) the one or more omega-3 fatty acids constitute at least about 10 wt % of the composition; (iii) the one or more gelling agents constitute less than 5 wt % of the composition and are selected from the group consisting of xanthan gum, locust bean gum, gellan gum, guar gum, pullulan, konjac flour, kappa-carrageenan, iota-carrageenan, gum tragacanth, and combinations thereof; and the composition has a Young's modulus (Pa/% strain) of from about 10 to about 95, and/or the composition has a Young's modulus (Pa/% strain) per unit composition surface area of from about 0.25 Pa/cm$^2$ to about 10 Pa/cm$^2$.

In further embodiments, the present invention is directed to an aqueous omega-3 fatty acid gel composition, the composition comprising water, one or more gelling, and one or more omega-3 fatty acids, wherein: (i) water constitutes at least 30 wt % of the composition; (ii) the one or more omega-3 fatty acids constitute at least about 10 wt % of the composition; (iii) the one or more gelling agents constitute less than 5 wt % of the composition and are selected from the group consisting of xanthan gum, locust bean gum, gellan gum, guar gum, pullulan, konjac flour, kappa-carrageenan, iota-carrageenan, gum tragacanth, and combinations thereof; and (iv) the composition has a gel strength per unit composition surface area is from about 0.1 to about 1.75 kPa/cm$^2$.

In further embodiments, the present invention is directed to an aqueous omega-3 fatty acid gel composition, the composition comprising water, one or more gelling, and one or more omega-3 fatty acids, wherein: (i) water constitutes at least 30 wt % of the composition; (ii) the one or more omega-3 fatty acids constitute at least about 10 wt % of the composition; (iii) the one or more gelling agents constitute less than 5 wt % of the composition and are selected from the group consisting of xanthan gum, locust bean gum, gellan gum, guar gum, pullulan, konjac flour, kappa-carrageenan, iota-carrageenan, gum tragacanth, and combinations thereof; and (iv) the composition has an extensibility of from about 50% to about 90%.

In even further embodiments, the present invention is directed to an aqueous gel emulsion, the emulsion comprising a lipophilic phase dispersed within a gelled aqueous phase, and an emulsifier, wherein the lipophilic phase comprises a lipophilic active ingredient, and the gelled aqueous phase comprises water and one or more gelling agents.

In still further embodiments, the present invention is directed to an aqueous gel emulsion, the emulsion comprising a lipophilic phase dispersed within a gelled aqueous phase, an emulsifier, and a lipophilic active ingredient dispersed within the lipophilic phase, wherein: water constitutes at least 30 wt % of the composition; and (i) the composition has a Young's modulus (Pa/% strain) of from about 10 to about 95; and/or (ii) the composition has a Young's modulus (Pa/% strain) per unit composition surface area of from about 0.25 Pa/cm$^2$ to about 10 Pa/cm$^2$.

In even further embodiments, the present invention is directed to an aqueous gel emulsion, the emulsion comprising a lipophilic phase dispersed within a gelled aqueous phase, an emulsifier, and a lipophilic active ingredient dispersed within the lipophilic phase, wherein: water constitutes at least 30 wt % of the composition; and the composition has a gel strength per unit composition surface area is from about 0.1 to about 1.75 kPa/cm$^2$.

In still further embodiments, the present invention is directed to an aqueous gel emulsion, the emulsion comprising a lipophilic phase dispersed within a gelled aqueous phase, an emulsifier, and a lipophilic active ingredient dispersed within the lipophilic phase, wherein: water constitutes at least 30 wt % of the composition; and the composition has an extensibility of from about 50% to about 90%.

In further embodiments, the present invention is directed to an aqueous gel emulsion, the emulsion comprising a lipophilic phase dispersed within a gelled aqueous phase, an emulsifier, and a lipophilic active ingredient dispersed within the lipophilic phase, wherein: syneresis of the composition during storage under ambient conditions for 90 days is less than about 10%.

In even further embodiments, the present invention is directed to a multi-layer aqueous gel composition for the delivery of one or more active ingredients, the composition comprising a first gel layer having a top surface and a bottom surface, and a second gel layer having a top surface and a bottom surface, the bottom surface of the second gel layer being applied to the top surface of the first gel layer thereby forming an integral multi-layer structure, wherein: (i) the first gel layer comprises water, one or more gelling agents, and a first active ingredient; and (ii) the second gel layer comprises water, one or more gelling agents, and a second active ingredient, wherein at least a portion of the second active ingredient is coated, thereby providing the second active ingredient with a release profile different than the release profile of the first active ingredient.

Other objects and features will be in part apparent and in part pointed out hereinafter.

BRIEF DESCRIPTION OF THE DRAWINGS

FIG. 5C provides the results of model esophagus testing as described in Example 5.

DETAILED DESCRIPTION OF THE PREFERRED EMBODIMENTS

Figure 1:
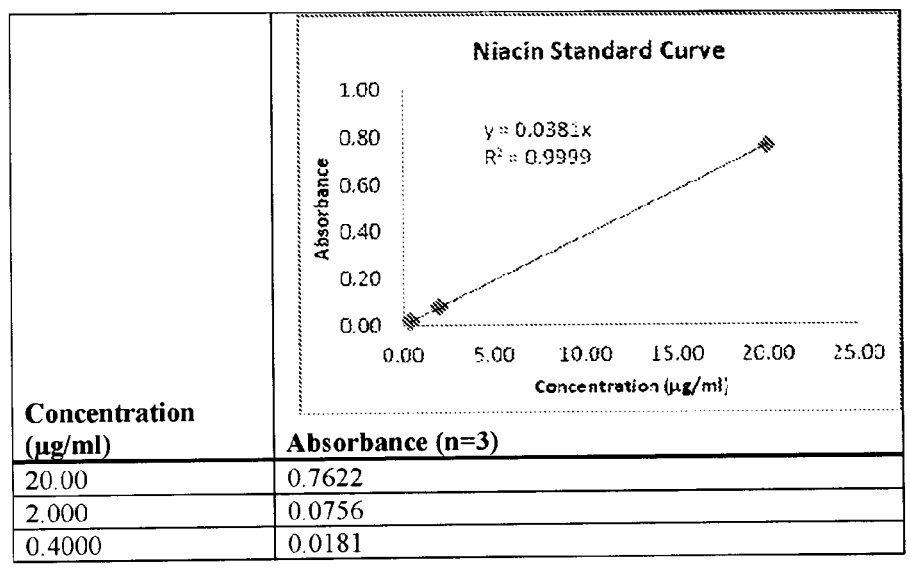
FIGS. 1 and 2 provide the results of niacin dissolution testing described in Example 2.

Described herein are gelling agent-based oral dosage forms suitable as a drug delivery system for administering a variety of active ingredients. One advantage of the dosage forms is ease of administration. The compositions of the present invention provide a dosage form that is easily consumed. In fact, the dosage forms of the present invention may be consumed by passing through the mouth of the subject without chewing and with very little effort in swallowing by the subject, much like one would swallow an oyster or small block of dessert gel. However, typically most consumers may exert at least some effort by chewing the dosage form. Once ingested and chewing begins, the dosage form readily takes on a liquid mouthfeel and passes through the mouth of the subject with little, if any, swallowing effort on the part of the subject. In this manner, the gel may be referred to as a "chewable liquid." Also, as detailed elsewhere herein, the dosage forms of the present invention typically contain a significant fraction of water. This high water content contributes to the ease of administration of the dosage forms of the present invention. This ease of administration provides significant advantages with respect to any subject and for use with a variety of active agents. In addition, and regardless of the ease of administration, compositions of the present invention advantageously allow for incorporation of higher active contents than conventional gelling agent-based dosage forms. For example, as detailed herein, in various embodiments, the dosage forms include an active ingredient(s) in a proportion of at least about 0.1 g active ingredient per g composition, or at least about 0.2 g active ingredient per g composition.

Another advantage of the gelling agent-based dosage forms of the present invention is relatively low formation of free water, referred to as syneresis. Low syneresis allows for ease in handling the gelling agent-based dosage form. In addition, low syneresis provides for a storage-stable dosage form the composition of which does not change significantly over time. Advantageously, and in the case of dosage forms containing pharmaceutically or biologically active ingredients this provides for a dosage form that retains the desired and prescribed concentration of active agent for a significant storage period.

Additionally, and alternatively in combination with the low syneresis, the gels of the present invention exhibit suitable structural integrity (e.g., gel strength) to provide stability, but do not exhibit such a rigid structure that makes the gels unbreakable during consumption or pose a choking hazard.

The gelling agent-based dosage forms of the present invention are also advantageously thermally stable such that that the composition (e.g., active ingredient content) is not degraded during storage under normal ambient conditions. For example, the present compositions generally exhibit higher melting points than gelatin-based compositions and, thus, are more stable during storage (e.g., may not require refrigeration) and/or are more stable during use under conditions where the temperature of the composition may be raised (e.g., during transport or storage or use by a consumer).

The present invention is further directed to gels that are in the form of an emulsion (e.g., "emulsion gels") that are generally prepared by dispersing an oil-based phase (e.g., lipophilic phase) within an aqueous, gelled water-based phase. As detailed herein, such gels may incorporate one or more components (e.g., flavor modifying ingredients) that may provide a taste-masked emulsion gel that may be used to mask the taste of poorly tasting active ingredients or active ingredients that are malodorous, in particular lipophilic active ingredients.

As also detailed herein, various embodiments of the present invention are directed to omega-3 fatty acid-containing gels exhibiting one or more of the advantageous features of the gels of the present invention.

The present invention is also directed to multi-layer gels that are prepared by combining a first gel layer and a second gel layer, and may contain one or more active ingredients. For example, in certain embodiments the multi-layer gels contain acetaminophen and may be prepared to provide different release profiles of acetaminophen from each layer of the gel.

I. Compositions

Generally, the gelling agent-based dosage forms of the present invention include water, an active ingredient, and one or more gelling agents. In addition to these components, the dosage forms also include various components that may contribute to desired characteristics of the gel. For example, it has been discovered that various components may be incorporated that contribute primarily to minimizing the formation of free water, or syneresis, of the gel. In this manner, certain components of the gel are referred to herein as a "syneresis controlling agent." It has further been discovered that various components may be incorporated that contribute to improved rheological properties of the gel. Thus, in this manner, certain components of the gel are referred to as a "rheology modifier" or a "rheology modification component." Although certain components have been discovered to provide such characteristics, it is to be understood that such components may likewise contribute to gel formation and, in this manner, may also properly be referred to as, for example, a "gelling agent." Thus, designating a component as a "gelling agent," "syneresis controlling agent," "rheology modifier," etc. does not exclude this component from providing other effect(s).

Generally, the compositions of the present invention include at least one gelling agent. Suitable gelling agents include various polysaccharides (e.g., galactomannans and glucomannans) selected from the group consisting of xanthan gum, locust bean gum, gellan gum, guar gum, gum arabic, gum ghatti, tara gum, karaya gum, pullulan, agar, alginate, konjac flour, pectin, kappa-carrageenan, iota-carrageenan, lambda-carrageenan, methyl cellulose, ethyl hydroxyethyl cellulose, ethyl methyl cellulose, hydroxypropyl cellulose, hydroxypropyl methyl cellulose, sodium carboxyethylcellulose, and combinations thereof.

In various embodiments, at least one gelling agent is selected from the group consisting of xanthan gum, locust bean gum, gellan gum, guar gum, pullulan, konjac flour, kappa-carrageenan, iota-carrageenan, and combinations thereof.

In certain embodiments, the composition includes: (i) xanthan gum, locust bean gum, and gellan gum; or (ii) xanthan gum, locust bean gum, and gellan gum, and pullulan; or (iii) xanthan gum, locust bean gum, and konjac flour; or (iv) xanthan gum, locust bean gum, and kappa-carrageenan; or (v) xanthan gum, locust bean gum, pullulan, and kappa-carrageenan; or (vi) locust bean gum, pullulan, and kappa-carrageenan; or (vii) xanthan gum, locust bean gum, and pullulan; or (viii) xanthan gum, locust bean gum, and iota-carrageenan; or (ix) xanthan gum, pullulan, and iota-carrageenan.

Generally, one or more of the gelling agent(s) constitute at least about 0.1 wt % or at least about 0.25 wt % of the composition. Further, generally, one or more of the gelling agent(s) constitute less than about 1 wt % or less than about 0.75 wt % of the composition. Thus, typically, one or more of the gelling agent(s) constitute from about 0.1 to about 1 wt % of the composition, or from about 0.25 to about 0.75 wt % of the composition.

In addition to water and active ingredients, as detailed elsewhere herein, the compositions of the present invention typically include various other components, including sweeteners, flavorants, coloring agents, and preservatives. Accordingly, the portion of the composition provided by the one or more gelling agents may be referred to as the base of the composition as it includes the components contributing to substantially, if not nearly all gel formation.

In addition to the one or more gelling agents, compositions of the present invention typically include at least one component that provides desired rheological properties (e.g., desirable gel strength). Such a component may be referred to as a rheology modifier. In various embodiments, a rheology modifier selected from the group consisting of xanthan gum, locust bean gum, guar gum, methyl cellulose, and combinations thereof, is included in the composition. Often, the rheology modifier is xanthan gum. A rheology modifier generally constitutes at least about 0.1 wt % or at least about 0.25 wt % of the composition. Further, generally, a rheology modifier constitutes less than about 1 wt % or less than about 0.75 wt % of the composition. Thus, typically, a rheology modifier constitutes from about 0.1 to about 1 wt % of the composition, or from about 0.25 to about 0.75 wt % of the composition. As detailed below, the compositions of the present invention are suitable for use in connection with a variety of active ingredients. The precise composition that may provide optimum performance and rheological properties may depend on the particular active ingredient to be incorporated. For example, the selection of the rheology modifier and/or its concentration may be modified depending on the active ingredient to be incorporated and/or the nature of the active (e.g., solubility).

As noted, compositions of the present invention advantageously exhibit relatively low syneresis. It is currently believed that one component of the composition contributes at least a substantial portion of syneresis control. Such a component may be referred to as a "syneresis controlling agent." For example, in the case of compositions including iota-carrageenan and locust bean gum inclusion of tragacanth controls syneresis. However, it is to be understood that the present invention is not limited to a particular syneresis controlling agent, generally or in combination with a particular combination of other components of the composition (e.g., the one or more gelling agents). Depending on the other components of the composition, a suitable syneresis controlling agent may be selected utilizing methods known in the art for preparing gelling agent-based compositions and for determining syneresis, including the methods detailed in the working examples of the present application.

Generally, and in accordance with the foregoing, a syneresis controlling agent is selected from various suitable polysaccharides (e.g., those listed above as suitable gelling agents). Typically, the syneresis controlling agent is selected from the group consisting of konjac flour, gum tragacanth, pullulan, gellan gum, and combinations thereof. A syneresis controlling agent generally constitutes at least about 0.1 wt % or at least about 0.25 wt % of the composition. Further, generally, a syneresis controlling agent constitutes less than about 1 wt % or less than about 0.75 wt % of the composition. Thus, typically, a syneresis controlling agent constitutes from about 0.1 to about 1 wt % of the composition, or from about 0.25 to about 0.75 wt % of the composition.

Various preferred embodiments of the present invention are directed to compositions including one or more of the above-prescribed gelling agents, along with at least one of the prescribed syneresis controlling agents and rheology modifiers. As noted, the portion of the composition constituted by the gelling agents is often referred to as the base, as it includes at least a significant portion of the components that contribute to gel formation. However, as noted above, it is to be understood that components designated as syneresis controlling agents and/or rheology modifiers may likewise contribute to gel formation.

In certain embodiments, the one or more gelling agents comprise locust bean gum and iota-carrageenan, the rheology modifier comprises xanthan gum, and the syneresis controlling agent comprises gum tragacanth. In accordance with such embodiments, typically locust bean gum constitutes from 0.1 to 1 wt % of the composition (e.g., from about 0.2 to about 0.6 wt %, or from about 0.25 to about 0.4 wt %), iota-carrageenan constitutes from about 0.1 to about 1 wt % of the composition (e.g., from about 0.2 to about 0.6 wt %, or from about 0.25 to about 0.4 wt %), xanthan gum constitutes from about 0.1 to about 2 wt % (e.g., from about 0.2 to about 0.6 wt % or from about 0.25 to about 0.4 wt %) of the composition, and gum tragacanth constitutes from about 0.1 to about 1 wt % (e.g., from about 0.2 to about 0.5 wt %) of the composition.

In other embodiments, the one or more gelling agents comprise locust bean gum and iota-carrageenan, the rheology modifier comprises xanthan gum, and the syneresis controlling agent comprises konjac flour. In accordance with such embodiments, typically locust bean gum constitutes from about 0.1 to about 1 wt % (e.g., from about 0.2 to about 0.6 wt %, or from about 0.25 to about 0.4 wt %) of the composition, iota-carrageenan constitutes from about 0.1 to about 1 wt % (e.g., from about 0.2 to about 0.6 wt %, or from about 0.2 to about 0.4 wt %) of the composition, xanthan gum constitutes from about 0.1 to about 2 wt % (e.g., from about 0.1 to about 1 wt %, or from about 0.2 to about 0.6 wt %) of the composition, and konjac flour constitutes from about 0.1 to about 1 wt % (e.g., from about 0.1 to about 0.6 wt %, or from about 0.1 to about 0.3 wt %) of the composition.

In various other embodiments, the one or more gelling agents comprise locust bean gum and iota-carrageenan, the rheology modifier comprises xanthan gum, and the syneresis controlling agent comprises konjac flour and tragacanth. In accordance with these embodiments, typically locust bean gum constitutes from about 0.1 to about 1 wt % (e.g., from about 0.2 to about 0.6 wt %, or from about 0.25 to about 0.4 wt %) of the composition, iota-carrageenan constitutes from about 0.1 to about 1 wt % (e.g., from about 0.2 to about 0.6 wt %, or from about 0.25 to about 0.4 wt %) of the composition, xanthan gum constitutes from about 0.1 to about 2 wt % (e.g., from about 0.1 to about 1 wt %, or from about 0.2 to about 0.4 wt %) of the composition, konjac flour constitutes from about 0.1 to about 1 wt % (e.g., from about 0.1 to about 0.8 wt %, or from about 0.1 to about 0.4 wt %) of the composition, and gum tragacanth constitutes from about 0.1 to about 1 wt % (e.g., from about 0.1 to about 0.8 wt %, or from about 0.1 to about 0.4 wt %) of the composition.

Generally in accordance with the above-described embodiments in which the gelling agents comprise locust bean gum and iota-carrageenan, the weight ratio of locust bean gum to iota-carrageenan is from about 40:60 or from about 60:40, and typically from about 45:55 to about 55:45. Various compositions also include locust bean gum as a gelling agent, a rheology modifier comprising xanthan gum, and a syneresis controlling agent comprising konjac flour. Typically in accordance with such embodiments, locust bean gum constitutes from about 0.1 to about 1 wt % (e.g., from about 0.2 to about 0.6 wt %, or from about 0.2 to about 0.4 wt %) of the composition, xanthan gum constitutes from about 0.1 to about 2 wt % (e.g., from about 0.2 to about 0.6 wt %, or from about 0.2 to about 0.4 wt %) of the composition, and konjac flour constitutes from 0.1 to 1 wt % of the composition (e.g., from about 0.2 to about 0.6 wt %, or from about 0.2 to about 0.4 wt %).

Further advantageous compositions of the present invention include locust bean gum and kappa-carragenan as gelling agents, xanthan gum as a rheology modifier, and pullulan as a syneresis controlling agent. Typically in such compositions, locust bean gum constitutes from about 0.1 to about 1 wt % (e.g., from about 0.2 to about 0.6 wt %, or from about 0.2 to about 0.4 wt %) of the composition, kappa-carrageenan constitutes from about 0.1 to about 1 wt % (e.g., from about 0.2 to about 0.6 wt %, or from about 0.2 to about 0.4 wt %) of the composition, xanthan gum constitutes from about 0.1 to about 2 wt % (e.g., from about 0.2 to about 1 wt %, or from about 0.2 to about 0.4 wt %) of the composition, and pullulan constitutes from about 0.1 to about 1 wt % (e.g., from about 0.2 to about 0.6 wt %, or from about 0.2 to about 0.4 wt %) of the composition.

Often gellan gum or carrageenan is incorporated as a gelling agent, along with locust bean gum and a rheology modifier that comprises xanthan gum. In accordance with such embodiments, locust bean gum typically constitutes from about 0.1 to about 1 wt % (e.g., from about 0.2 to about 0.6 wt %, or from about 0.2 to about 0.4 wt %) of the composition, xanthan gum constitutes from about 0.1 to about 2 wt % (e.g., from about 0.1 to about 1 wt %, or from about 0.2 to about 0.4 wt %) of the composition, and gellan gum or carrageenan constitutes from about 0.1 to about 1 wt % (e.g., from about 0.2 to about 0.6 wt %, or from about 0.2 to about 0.4 wt %) of the composition.

In accordance with the foregoing, in various embodiments the components identified as the one or more gelling agents, syneresis controlling agents, and rheology modifiers are essentially the only components of the composition providing the desired effect. Thus, the one or more gelling agents, syneresis controlling agents, and rheology modifiers consist essentially of the prescribed components and another component of the composition does not contribute in any significant manner to the desired effect.

Various embodiments of the present invention incorporate a source of metal cations (e.g., calcium, sodium, or potassium). Generally, the presence of the source of metal cations provides a pH of the mixture formed during gel preparation and/or the final gel composition within a desired range that provides one or more advantages. The desired pH range of the gel composition component mixture and/or final gel composition is typically from about 5 to about 9 and, more typically, from about 6 to about 8. In various embodiments, the presence of a metal cation and resulting desired pH promotes gel formation in the presence of certain gelling agents, rheology modifiers, and/or syneresis controlling agents. For example, it is currently believed that the presence of a source of potassium ions promotes gel formation in the case of kappa-carrageenan as a gelling agent. By way of further example, it is currently believed that the presence of a source of calcium ions promotes gel formation in the case of iota-carrageenan as a gelling agent. The presence of this component is currently believed to provide the gel with one or more advantageous properties. For example, for certain combinations of components (e.g., compositions including carrageenan as a gelling agent) acidic gels at pHs below the preferred ranges have been observed to lose gel strength, or melt. In addition, for these and other combinations of components, basic gels at pHs above the desired ranges have been observed to exhibit undesired taste properties.

In various embodiments, the composition comprises a source of potassium ions, a source of sodium ions, a source of calcium ions, or a combination thereof provided by a water-soluble salt. Suitable sources of sodium ions generally include water-soluble sodium salts including, for example, sodium chloride, sodium citrate, sodium acetate, and combinations thereof. Suitable sources of calcium ions include water-soluble calcium salts including, for example, calcium acetate, calcium chloride, calcium carbonate, calcium ascorbate, and combinations thereof. Suitable sources of potassium ions include water soluble-soluble potassium salts including, for example, potassium chloride, potassium acetate, and combinations thereof. Typically, the source(s) of metal ions is present in a proportion of from about 0.1 to about 1 wt % of the composition, more typically in a proportion of from about 0.2 to about 0.6 wt % and, still more typically, from about 0.2 to about 0.4 wt %. For example, in those embodiments in which the composition comprises locust bean gum and iota-carrageenan, the composition typically further comprises a source of calcium ions (e.g., $CaCl_2$) in a proportion of from about 0.1 to about 1 wt % of the composition and, more typically, in a proportion of from about 0.2 to about 0.6 wt %. By way of further example, in those embodiments in which the composition comprises kappa-carragenenan and locust bean gum, the composition typically comprises a source of potassium (e.g., potassium chloride) in a proportion of from about 0.1 to about 1 wt % of the composition and, more typically, in a proportion of from about 0.2 to about 0.6 wt %.

As noted above, the compositions of the present invention are easily administered, or consumed and, more particularly, easily swallowed or chewed with very little effort on the part of the consumer. In this manner, as noted, the compositions of the present invention may be referred to as a "chewable liquid." One indicator of this ease of administration in this manner is the water content of the compositions of the present invention. Generally, the water content of an active ingredient-containing composition of the present invention is at least about 20 wt %, at least about 30 wt %, at least about 40 wt %, at least about 50 wt %, or at least about 60 wt %. Typically, water constitutes from about 20 to about 70 wt %, from about 30 to about 60 wt %, or from about 30 to about 50 wt %. In other embodiments, water may constitute from about 40 to about 70 wt %, or from about 50 to about 60 wt %.

Generally, the weight ratio of water to the one or more gelling agents (e.g., any and all of the combinations listed above) is at least about 5:1, a least about 10:1, at least about 15:1, at least about 20:1, at least about 25:1, or at least about 30:1. Typically, the weight ratio of water to the one or more gelling agents is from about 5:1 to about 50:1, from about 10:1 to about 45:1, from about 15:1 to about 40:1, from about 20:1 to about 40:1, or from about 25:1 to about 35:1.

Advantageously, the gels of the present invention are suitable for delivering relatively large dosages of active ingredients. Additionally or alternatively, the gels of the present invention are suitable for delivering more than one active ingredient. Generally in accordance with the present invention, the active ingredient(s) constitutes at least about 5 wt %, at least about 10 wt %, or at least about 15 wt %. of the gel. Typically, the active ingredient(s) constitutes at least about 20 wt % and, more typically, at least about 25 wt % of the gel. Further in accordance with the present invention, the active ingredient(s) constitutes from about 5 to about 50 wt %, from about 10 to about 45 wt %, or from about 20 to about 40 wt % of the gel.

The loading of one or more active ingredient per unit gel weight is also an advantageous property of gels of the present invention. In fact, the gels are currently believed to be suitable for incorporating higher active ingredient loadings than conventional gelling agent-based dosage forms, but while also exhibiting suitable gel strength and also relatively low formation of free water (i.e., syneresis). Typically, the active ingredient loading is at least about 0.05 g active ingredient per gram composition and, more typically, at least about 0.07 g active ingredient per gram composition. Preferably, the active ingredient loading is at least about 0.1 g active ingredient per gram composition, more preferably at least about 0.2 g active ingredient per gram composition and, even more preferably, at least about 0.3 g active ingredient per gram composition. Thus, typically, the active ingredient loading is from about 0.05 to about 0.5 g active ingredient per gram composition and, more typically, from about 0.1 to about 0.4 g active ingredient per gram composition.

Various embodiments of the present invention are directed to dosage forms comprising a combination of gelling agents including konjac (i.e., konjac flour), locust bean gum, and xanthan gum. Although they form a gel, when xanthan and konjac flour are combined as gelling agents along with a salt, syneresis may be observed. As noted above, salts are preferably included in gelling agent-based dosage forms in order to provide desired gel properties. For example, inclusion of the metal cations as buffering salts also controls the pH of the gel composition. In accordance with the present invention it has been discovered that when locust bean gum is included in a gel along with konjac flour and xanthan gum, little or no syneresis is observed. It is currently believed that the konjac flour and xanthan gum provide the primary gelling function while the locust bean gum provides the primary syneresis inhibition. Although the locust bean gum is the primary contributor to syneresis inhibition, it is to be understood that locust bean gum also contributes to gel formation. Thus, various embodiments of the present invention are directed to pH-controlled, salt-containing gelling agent-based dosage forms including a combination of konjac flour, xanthan gum, and locust bean gum that exhibit little, if any syneresis. In addition, this combination of gelling agents is also believed to provide gels of desired physical properties regardless of any inhibition of syneresis in the presence of salts. The konjac/xanthan/locust bean gum formulations of the present invention thus represent an advance in the art by exhibiting one or of the properties noted below (e.g., gel strength, extensibility, etc.). The konjac/xanthan/locust bean gum formulations are also advantageously thermally stable.

Further embodiments of the present invention are directed to compositions including a combination of xanthan gum, iota-carrageenan, and locust bean gum. The compositions may optionally also include konjac and/or tragacanth.

Additional embodiments of the present invention include kappa-carrageenan, xanthan gum, and locust bean gum. These compositions may also include a source of potassium ions.

Further compositions of the present invention include a combination of gellan gum, xanthan gum, and locust bean gum. These compositions have been discovered to exhibit advantageous gel strengths. In particular, these compositions exhibit gel strengths that are suitable to provide stability and integrity to the composition, but they are also sufficiently brittle, or exhibit a break point such that excessive force is not required to rupture the composition. In this manner, these compositions do not represent a choking hazard.

The compositions of the present invention also typically include one or more additional components selected from the group consisting of preservatives, flavorants, sweeteners, coloring agents, and combinations thereof.

Suitable preservatives include those generally known in the art including, for example, methyl paraben, ethyl paraben, propyl paraben, sodium benzoate, glycerol, and combinations thereof.

Suitable flavorants include peppermint, oil of wintergreen, natural and artificial fruit flavorings, and combinations thereof.

Suitable sweeteners include sucrose, lactose, saccharin, sucralose, xylitol, mannitol, and combinations thereof.

Suitable coloring agents include those generally known in the art including, for example, FD&C dyes and lakes.

II. Gel Characteristics

Compositions of the present invention preferably exhibit various properties that indicate an advantageous composition. These properties are indicative of, for example, suitable storage stability, ease in handling (e.g., structural stability), ease of administration and avoiding a choking hazard, low syneresis, and/or maintaining relatively constant active ingredient concentration.

Generally, in connection with active ingredient-containing dosage forms, the active ingredient content preferably does not change by any appreciable portion during storage under ambient conditions. Ambient conditions typically involve storing the composition in a suitable container under ambient temperature (e.g., approximately 25° C.) and pressure conditions. Typically, the variation in active ingredient during storage under ambient conditions is no more than about 10%. In particular, the active ingredient preferably does not vary by more than 10% during storage periods of up to 90 days. One issue that impacts active ingredient concentration is formation of free water, or syneresis, of the composition during storage. For example, in connection with water-soluble actives, active ingredient content may be reduced to an unacceptable degree if relatively high syneresis is observed. Loss of water in connection with compositions including insoluble active ingredients is also not desired since if water loss reaches a certain level the overall mass of the composition may be decreased such the active ingredient concentration may increase to an unacceptable degree. Water loss from compositions of the present invention is also undesired as it raises issues with processing and packaging of the compositions, and may also make the composition difficult to handle by a consumer.

Formation of free water or syneresis may be determined in accordance with methods known in the art, including the examples provided herein. Generally, syneresis (i.e., formation of free water) from compositions of the present invention is no more than about 10%, no more than about 7%, or no more than about 5% of when the composition is stored under ambient conditions for up to 90 days (e.g., at least 60 days). As provided herein, percent syneresis refers to the ratio of the mass of water lost from the gel composition as a proportion of the initial gel composition weight. Preferably, syneresis is no more than about 5% or no more than about 3% when the composition is stored under ambient conditions for up to 90 days (e.g., at least 60 days). In this manner, the active ingredient content does not vary to any significant, undesired degree based on moisture loss from the gel.

In addition to overall formation of free water, or syneresis, compositions of the present invention also exhibit low syneresis when expressed as a function of the total exposed surface area of the composition. For example, the syneresis is generally no more than about 15 mg water/cm$^2$ composition surface area, no more than about 10 mg water/cm$^2$ composition surface area, or no more than about 5 mg water/cm$^2$ composition surface area when the composition is stored under ambient conditions for up to 90 days. Typically the syneresis is no more than about 4 mg water/cm$^2$ composition surface area, more typically no more than about 2 mg water/cm$^2$ composition surface area and, still more typically, no more than about 1 mg water/cm$^2$ composition surface area when the composition is stored under ambient conditions for up to 90 days.

Certain features of the compositions of the present invention identified are rheological properties that indicate, for example, structural stability of the compositions such that the compositions may be packaged and handled without breaking or loss of any portion(s) of the composition. These properties may be determined utilizing a suitable texture analyzer known to those skilled in the art. For example, the data provided in the working examples herein were gathered utilizing a TA TXT texture analyzer. However, it is currently believed that the gel properties of the compositions of the present invention are not equipment-specific such that the properties detailed herein apply to compositions analyzed utilizing the prescribed equipment, but also apply to compositions utilizing other suitable equipment known for use in connection with generating such data.

One measure of the structural integrity of the composition is its gel strength. Gel strength is determined by subjecting the composition to a force and plotting the stress to which the composition is subjected (force, Pa) versus the strain which the composition undergoes (extensibility, %). This plot provides a stress vs. strain curve. The composition may be subjected to a force that results in a rupture of the gel, with the point at which the gel ruptures on the stress vs. strain curve referred to as the rupture point. Thus, the gel strength of a composition may be expressed in terms of its gel strength at its rupture point (i.e., the force to which the composition may be subjected prior to rupture). Additionally, the extensibility of the composition may be expressed as the percent to which the gel deforms from its original dimensions prior to rupture. Generally, the gel strength of a composition of the present invention at its rupture point is at least about 1 kPa, at least about 10 kPa, or at least about 15 kPa. Typically, the gel strength of the gel at its rupture point is at least about 25 kPa, at least about 40 kPa, or at least about 50 kPa. Typically, the gel strength of a composition of the present invention at its rupture point is from about 4 kPa to about 70 kPa, from about 10 kPa to about 60 kPa, or from about 20 kPa to about 50 kPa.

More particularly, generally the gel strength of the compositions of the present invention is at least about 0.025 kPa/cm$^2$ surface area, at least about 0.25 kPa/cm$^2$ surface area, at least about 0.4 kPa/cm$^2$ surface area, at least about 0.6 kPa/cm$^2$ surface area, or at least about 1 kPa/cm$^2$ surface area. Typically, the gel strength of the composition is from about 0.1 to about 1.75 kPa/cm$^2$ surface area, from about 0.25 to about 1.5 kPa/cm$^2$ surface area, or from about 0.5 to about 1.25 kPa/cm$^2$ surface area.

Compositions of the present invention generally exhibit an extensibility of at least about 50%, at least about 60%, or at least about 70%. Often, the gels exhibit an extensibility of at least about 80%, or at least about 90%. Typically, the compositions of the present invention exhibit extensibility of from about 50 to about 80% and, more typically, of from about 60 to about 80%.

Typically, the compositions of the present invention exhibit an extensibility of at least about 1%/cm$^2$ surface area, at least about 1.5%/cm$^2$ surface area, or at least about 2%/m$^2$ surface area. Generally, the compositions exhibit an extensibility of from about 1 to about 2%/m$^2$ surface area, or from about 1.5 to about 2%/m$^2$ surface area.

Gel compositions of the present invention may also be characterized by the rupture point on a stress-strain curve when a downward force of from about 0.1 lbs to about 2.2 lbs is applied to the gel composition. Generally, the stress-strain curve of the gel composition under such conditions exhibits a rupture point of from about 150 to about 4000 (gel strength-Pa)/(extensibility-%) or from about 200 to about 200 (Pa/%).

An additional rheological property indicating advantageous features of the gels of the present invention is the Young's modulus. Generally, the Young's modulus is defined as the slope of the stress vs. strain curve generated during texture analysis. The higher the slope, the less deformable the gel and, conversely, the lower the slope the more deformable the gel. Gels which deform little, if any are commonly referred to as non-deformable gels. Gels which are easily deformed and easily lose structural integrity are commonly referred to as melting gels. Gels of the present invention advantageously exhibit a Young's modulus (i.e., slope of the stress vs. strain curve) higher than those of melting gels and lower than those of non-deformable gels. In particular, the Young's modulus is currently believed to increase at a greater rate as compared to less structurally stable melting gels as the strain placed on the gel during texture analysis. Thus, the present gels exhibit greater structural integrity than the melting gels while also exhibiting some degree of deformation, which contributes to the ease of administration highlighted elsewhere herein and also minimizes choking risks. Further advantageously, as detailed elsewhere herein the present gels exhibit such structural features while exhibiting low syneresis.

Generally, the gels of the present invention exhibit a Young's modulus (Pa/% strain) of from about 10 to about 95 or from about 10 to about 75. Typically, the gels exhibit a Young's modulus (Pa/% strain) of from about 10 to about 60, more typically from about 20 to about 50 and, still more typically, from about 25 to about 40.

Typically, the Young's modulus of the composition (Pa/% strain) per unit composition surface area is from about 0.25 to about 10 $Pa/cm^2$, from about 1 to about 10 $Pa/cm^2$, from about 1 to about 8 $Pa/cm^2$, or from about 3 to about 7 $Pa/cm^2$. Often, in other embodiments, the Young's modulus of the composition (Pa/% strain) per unit composition surface area is from about 0.25 $Pa/cm^2$ to about 2.5 $Pa/cm^2$, from about 0.25 $Pa/cm^2$ to about 2 $Pa/cm^2$, from about 0.25 $Pa/cm^2$ to about 1.5 $Pa/cm^2$, from about 0.5 $Pa/cm^2$ to about 1.2 $Pa/cm^2$.

As noted above, one advantage of the compositions of the present invention is ease of administration, or consumption. This ease of administration is observed qualitatively by a consumer as little, if any, effort is required to consume the gel composition. This feature may also be determined by testing of the gel composition under particular conditions. For example, the deformable gel composition may be introduced into an un-lubricated vertically-arranged cylinder having an inner diameter substantially equal to the deformed diameter of a cylindrical gel composition and the time for passage of the gel composition through the vertical cylinder under the force of gravity is observed. For example, typically when a cylindrical gel composition of the present invention is introduced into an un-lubricated cylinder having a length of 20 centimeters (cm) and an inner diameter substantially equal to the diameter of the cylindrical composition, the composition passes through the cylinder in no more than about 500 seconds, no more than about 400 seconds, no more than about 300 seconds, no more than about 200 seconds, no more than about 100 seconds, or no more than about 60 seconds. Additionally or alternatively, generally a cylindrical gel composition of the present invention generally passes through an un-lubricated cylinder having an inner diameter substantially equal to the diameter of the cylindrical composition at a rate of at least about 0.04 cm/sec, or at least about 0.2 cm/sec.

Gel compositions of the present invention may be molded or constructed into a variety of forms. The compositions are also deformable gels. Advantageously, the deformable gels of the present invention exhibit suitable strength and textural properties (e.g., gel strength), but are not so rigid such that there may be a risk of choking. Compositions of the present invention are also thermally reversible. In this manner, compositions of the present invention, or a portion thereof, may change state (e.g., melt) in response to temperature conditions, but also return to the gel state upon returning to temperature conditions in which the composition is in the form of a gel. In addition to being able to return to the gel form, if necessary, advantageously the compositions of the present invention may exhibit higher melting points than conventional gel-based compositions (e.g., gelatin-based dosage forms). These higher melting points provide stability during storage and also typically avoid the need for refrigeration during storage. Generally, the melting point of a gel-based composition of the present invention is at least about 40° C., at least about 45° C., or at least about 50° C.

Generally, the melting point of gel-based compositions of the present invention is less than about 90° C., less than about 85° C., less than about 80° C., less than about 75° C., or less than about 70° C. Typically in accordance with the present invention, the melting point of gel-based compositions of the present invention is from about 40° C. to about 90° C., more typically from about 45° C. to about 80° C. and, still more typically, from about 50° C. to about 75° C. Such melting points of the gels of the present invention provide suitable storage stability, while also providing thermal stability of the active ingredients to be incorporated into the compositions of the present invention.

Compositions of the present invention may be molded and packaged in a variety of forms including individual gels for oral consumption. For example, as noted above the gels are suitable as a drug delivery device that may be described as a "chewable liquid." Often the gels are in the form of individual dosages, similar to a tablet or lozenge of a desired shape and desired dimensions depending on the application and packaged individually and/or along with other individual dosage gels. The particular shape is not limited and may be, for example, generally cylindrical, spherical, oval, rectangular, or square. Generally, the volume of the gel composition may be at least about 1 $cm^3$, at least about 2 $cm^3$, or at least about 5 $cm^3$. Typically, the volume of gel compositions of the present invention is from about 1 to about 10 $cm^3$, from about 2 to about 10 $cm^3$, or from about 2 to about 8 $cm^3$. The total exposed surface area of the composition, regardless of its precise form or shape, is not narrowly critical, but generally is at least about 10 $cm^2$, at least about 20 $cm^2$, or at least about 30 $cm^2$. Typically, the total exposed surface area of the composition is from about 10 to about 60 $cm^2$, from about 20 to about 50 $cm^2$, or from about 35 to about 45 $cm^2$. The total mass of the gel composition is generally at least about 1 grams (g), at least about 2 g, or at least about 3 g. Often, the total mass of the gel composition is from about 1 to about 10 g, from about 2 to about 8 g, or from about 3 to about 6 g. Gel composition density is typically at least about 0.98, at least about 1.25, or at least about 1.5 g/mL. Gel composition density is also typically less than about 2.5 or less than about 2.0 g/mL.

As noted, the particular shape of the gels of the present invention is not limited and may be, for example, generally cylindrical, spherical, oval, rectangular, or square. In addition, the shape of the gel may be selected to be particularly desirable to a particular set of consumers. For example, in the case of children, the shape may be selected to correspond to those of characters well-known to children and/or any other shape generally appealing to children.

In certain embodiments, the gel is generally cylindrical having a diameter generally ranging from about 10 mm to about 30 mm, or from about 15 mm to about 25 mm; and a height generally ranging from about 5 mm to about 60 mm, or from about 15 mm to about 40 mm.

In certain other embodiments, the gel is generally spherical and having a radius generally of from about 5 mm to about 20 mm, or from about 10 mm to about 15 mm.

The gel may also be generally oval, generally having dimension of from about 10 mm to about 60 mm (e.g., about 20 to about 50 mm, or about 40 mm, or about 50 mm) in the longitudinal (i.e., longest) dimension; a crosswise (i.e., width) dimension of from about 10 mm to about 30 mm (e.g., about 20 mm); and a thickness of from about 5 to about 15 mm (e.g., about 10 mm).

The gels may also be generally rectangular having a length of from about 10 mm to about 50 mm, or from about 20 mm to about 40 mm; a width of from about 5 mm to about 30 mm, or from about 10 mm to about 20 mm; and a height of from about 5 mm to about 30 mm, or from about 10 mm to about 20 mm.

The gels may also be generally square having a length and width of from about 5 mm to about 40 mm or from about 10 mm to about 30 mm; and a height of from about 5 mm to about 40 mm.

In addition to gels designed for consumption as individual dosages (e.g., similar in size and shape to a lozenge or tablet or capsule), the gels may be formed into larger dosage and consumption forms. For example, the gels may be formed into cups generally of the size and shape suitable for providing individually packaged yogurts or puddings designed for consumption using a utensil such as a spoon. These gels may also be designed in squeezable containers suitable for consumption of the gel directly from the container and without the use of utensil. For example, in certain embodiments, the gel may be formulated into a cup or container having a volume of at least 1 ounce (oz), at least 2 oz, at least 3 oz, at least 4 oz, or even at least 5 oz, or greater. These containers may have volumes of from about 1 oz to about 12 oz, from about 2 oz to about 10 oz, or from about 3 oz to about 8 oz. For example, in certain embodiments the gels may be formed in a container (e.g., a cup) having a volume of from about 4 to about 6 oz. Such containers may be generally square, cylindrical, or rectangular. For example, certain container may be generally square and have dimensions of about 40 mm×40 mm×70 mm.

III. Method of Preparation

Generally, the compositions of the present invention are prepared by dispersing, or dissolving the gelling agent(s) (e.g., the components of the base contributing to at least substantially all gel formation) and any syneresis controlling agent and/or rheology modifier in a suitable liquid medium. In the following description of the method of preparation, the combination of these components is generally referred to as the "gelling agents."

In various embodiments, to promote dispersion, typically the gelling agents are combined and mixed with a dispersing agent prior to introduction into the liquid medium. Suitable dispersing agents include, for example, glycerin, propylene glycol, and combinations thereof. Typically, the total proportion of dispersing agent(s) in the liquid medium including the gelling agents and other components is less than about 5 wt %, less than about 4 wt %, less than about 3 wt %, or less than about 2 wt %. Generally, the weight ratio of dispersing agent (e.g., glycerin) to gelling agents is at least about 2:1, at least about 3:1, or at least about 4:1 (e.g., at least about 5:1).

The liquid medium is typically water, and preferably deionized water. Typically, the weight ratio of the liquid medium to the total proportion of gelling agents is at least about 90:1, more typically at least about 95:1 and, still more typically, at least about 98:1.

To promote dispersion, and preferably dissolution of the gelling agents throughout the liquid medium the resulting mixture is generally heated to a temperature of at least about 80° C., at least about 85° C., at least bout 90° C., or at least about 95° C. Typically, suitable dispersion or dissolution of the gelling agents throughout the liquid medium is provided by heating the mixture to a temperature of from about 80 to about 100° C. and more typically to a temperature of from about 85 to about 95° C. and (e.g., about 90° C.).

If necessary, the gelling agents/aqueous medium mixture may be agitated during heating to promote dispersion and dissolution of the gelling agents. It is currently believed that first dispersing the gelling agents in a dispersing medium allows for less severe agitation to provide dispersion throughout the liquid medium. This advantage is particularly beneficial in connection with large, commercial scale manufacture of the gels.

In addition to the gelling agents and active ingredients, the compositions typically include additional components such as preservatives, flavorants, coloring agents, and sweeteners. Also, as noted, often the compositions include a source of metal ions, typically a metal salt. Typically, the active ingredient and the additional components are added to the heated gelling agent(s)/liquid medium mixture in suitable proportions to provide the desired effect. The resulting mixture is then agitated to promote dispersion of these components. The manner and degree of agitation are not narrowly critical, but typically the mixture is agitated at from about 300 to about 800 revolutions per minute (rpm) utilizing suitable apparatus known in the art to provide dispersion of all components.

After suitable mixing of the mixture including the gelling agent(s), active ingredient(s), and additional components, this mixture is allowed to cool and a gel is formed. Generally, gel formation occurs upon cooling of this mixture to temperatures of less than about 55° C., less than about 50° C., or less than about 45° C. Typically, gel formation occurs upon cooling to temperatures of from about 25 to about 60° C., more typically from about 30 to about 55° C. and, still more typically, from about 45 to about 45° C.

The thus formed gel is then incorporated into any suitable container for storage, packaging, and distribution. The formed gel can also be sized as individual dosages for packaging.

As detailed elsewhere herein, the present invention in various aspects is directed to emulsion gels comprising a lipophilic phase dispersed within or throughout an aqueous, gelled phase. In accordance with such embodiments, a lipophilic, oil-based phase containing, for example, an oil-based active ingredient is prepared by combing the lipophilic active ingredient along with other components such as flavoring oils, and emulsifying components. Once the lipophilic phase is prepared, it is combined and dispersed within an aqueous phase prepared generally as described above. The proportions of the lipophilic phase and aqueous phase may generally be selected to provide the weight ratios of oil phase to aqueous phase detailed elsewhere herein and/or as shown in the accompanying Examples.

IV. Active Ingredients

Compositions of the present invention are suitable for use in connection with a variety of active ingredients, including pharmaceutically active ingredients (prescription and over-the-counter), nutraceuticals, vitamins, minerals, dietary supplements, and combinations thereof.

Suitable pharmaceutically active ingredients include the following. It is to be understood that reference to particular active ingredients herein includes pharmaceutically acceptable salts and derivatives thereof.

Central nervous system stimulants such as caffeine.

Non-steroidal anti-inflammatory drugs such as ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketorlac, acetyl salicylic acid, acetaminophen, and combinations thereof.

Antitussives such as ethylmorphine, dextromethorphan, pholcodine, codeine, hydrocodeine, and combinations thereof.

Expectorants such as acetylcysteine, bromhexine, emetine, guaiphenesin, ipecacuanha, saponins, and combinations thereof.

Decongestants such as phenylephrine, phenylpropanolamine, pseudoephedrine, and combinations thereof.

Antihistamines such as meclozine, cyclizine, chlorcyclizine, hydroxyzine, brompheniramine, chlorpheniramine, clemastine, cyproheptadine, dexchlorpheniramine, diphenhydramine, diphenylamine, doxylamine, mebhydrolin, pheniramine, tripolidine, azatadine, diphenylpyraline, methdilazine, terfenadine, astemizole, loratidine, cetirizine, and combinations thereof.

In various other embodiments, the active ingredient is a nutraceutical selected from the group consisting of α-carotene, β-carotene, leutine, lycopene, riboflavin, resveratrol, retinol, a polyunsaturated fatty acid (e.g., an omega fatty acid), and combinations thereof.

Suitable examples of omega-3 fatty acids include all-cis 7,10,13-hexadecatrienoic acid; all-cis-9,12,15-octadecatrienoic acid (alpha-linolenic acid, ALA); all-cis-6,9,12,15-octadecatetraenoic acid (stearidonic acid); all-cis-8,11,14,17-eicosatetraenoic acid (eicosatetraenoic acid); all-cis-5,8,11,14,17-eicosapentaenoic acid (eicosapentaenoic acid, EPA); all-cis-7,10,13,16,19-docosapentaenoic acid (clupanodonic acid, DPA); all-cis-4,7,10,13,16,19-docosahexaenoic acid (docosahexaenoic acid, DHA); all-cis-4,7,10,13,16,19-docosahexaenoic acid; all-cis-6,9,12,15,18,21-tetracosenoic acid (nisinic acid); and combinations thereof. In an exemplary embodiment, the omega-3 fatty acid is selected from the group consisting of ALA, DHA, EPA, DPA, and combinations thereof.

Examples of suitable omega-6 fatty acids include all-cis-9,12-octadecadienoic acid (linoleic acid); all-cis-6,9,12-octadecatrienoic acid (gamma-linolenic acid, GLA); all-cis-11,14-eicosadienoic acid (eicosadienoic acid); all-cis-8,11,14-eicosatrienoic acid (dihomo-gamma-linolenic acid, DGLA); all-cis-5,8,11,14-eicosatetraenoic acid (arachidonic acid, AA); all-cis-13,16-docosadienoic acid (docosadienoic acid); all-cis-7,10,13,16-docosatetraenoic acid (adrenic acid); all-cis-4,7,10,13,16-docosapentaenoic acid (docosapentaenoic acid); and combinations thereof.

Suitable examples of omega-9 fatty acids include cis-9-octadecenoic acid (oleic acid); cis-11-eicosenoic acid (eicosenoic acid); all-cis-5,8,11-eicosatrienoic acid (mead acid); cis-13-docosenoic acid (erucic acid), and cis-15-tetracosenoic acid (nervonic acid); and combinations thereof.

In still further embodiments, the active ingredient is a vitamin selected from the group consisting of retinol, retinal, carotenoids, thiamine, riboflavin, niacin, niacinamide, pantothenic acid, pyridoxine, pyridoxamine, pyridoxal, biotin, folic acid, folinic acid, cyanocobalamin, hydroxycobalamin, methylcobalamin, ascorbic acid, ergocalciferol, cholecalciferol, tocopherols, tocotrienols, phylloquinone, menaquinones, vitamin C, vitamin A, vitamin E, vitamin B12, vitamin K, menaquinone, menatetrenone, inositol, nicotinate, vitamin D, vitamin B6, pyridoxine, thiamine, pantothenic acid, and combinations thereof. The form of the vitamin may include salts of the vitamin, derivatives of the vitamin, compounds having the same or similar activity of a vitamin, and metabolites of a vitamin.

In further embodiments, the active ingredient is a mineral selected from the group consisting of potassium, chlorine, sodium, calcium, phosphorus, magnesium, zinc, iron, manganese, copper, iodine, selenium, chromium, molybdenum, and mixtures thereof. The composition may include one or more minerals or mineral sources. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and combinations thereof.

In various other embodiments, the active ingredient is a dietary supplement selected from the group consisting of glucosamine chondroitin, fish oil, coenzyme Q10 (CoQ10), and combinations thereof.

Advantageously, the active ingredient content of the compositions does not vary significantly over time such that the compositions of the present invention are storage-stable. Typically, the active ingredient content of the composition varies by less than about 10%, less than about 7%, less than about 5%, or less than about 3% during storage under ambient conditions for up to 3 months.

One advantageous feature of the compositions of the present invention is that they allow for incorporating relatively high active ingredient loadings. Generally, the compositions of the present invention are suitable for providing active ingredient dosages of at least about 100 mg/day, at least about 200 mg/day, at least about 400 mg/day, at least about 600 mg/day, at least about 800 mg/day, or even at least about 1000 mg/day. Typically, the compositions of the present invention provide active ingredient dosages of from about 100 mg/day to about 2000 mg/day, more typically from about 300 mg/day to about 1750 mg/day, and still more typically, from about 500 mg/day to about 1500 mg or from about 1000 mg/day to about 1500 mg/day (e.g., about 1200 mg/day).

Since the compositions of the present invention may be utilized to incorporate higher active ingredient loadings, single dosages of the compositions of the present invention may be utilized to provide higher dosages of active ingredient as compared to a single dosage of conventional gel-based dosage forms. Additionally or alternatively, single dosages of the compositions of the present invention may be utilized to provide equivalent, or even greater dosages as compared to dosages of conventional gel-based dosage forms that require multiple dosage forms.

Often consumers are required to take multiple tablets, capsules, or other dosage forms to receive the desired dose. Compositions of the present invention are suitable for providing a complete daily dosage in a single dose. For example, in connection with various dietary supplements (e.g., ascorbic acid or calcium ascorbate), often relatively high daily dosages are consumed (e.g., in excess of 1000 mg). Compositions of the present invention allow for administering such dosages in a single dosage form. Such compositions thus provide advantages in terms of convenience in administration and dosage regimens. Furthermore, as noted above, compositions of the present invention are easily consumed, even when used to deliver a relatively high dosage of active ingredient in a single dosage form. Compositions of the present invention may also be utilized to administer recommended daily dosages in a single dosage form in connection with various vitamins, minerals, oils (e.g., fish oil), acids (e.g., omega-3 fatty acids and omega-6 fatty acids), and specialty supplements (e.g., glucosamine chrondroitin and fiber supplements). Compositions of the present invention are also suitable for use as a multi-vitamin supplement, alone and in combination with other supplements.

By way of further example, in the case of non-steroidal anti-inflammatory drugs such as ibuprofen and naproxen the maximum daily dosage is from 1200-1500 mg. Often consumers take multiple dosages of multiple tablets to achieve the maximum daily dose. Compositions of the present invention are suitable for taking a single dosage form rather than multiple tablets at any one time. Moreover, for those patients that require the maximum daily dosage (e.g., arthritis patients taking steroidal anti-inflammatory drugs such as naproxen), achieving the maximum daily dosage requires administration of multiple tablets and often multiple tablets at multiple times. Compositions of the present invention may be utilized to provide dosages of, for example, 400-500 mg in a single dosage, or even a total of 1200-1500 mg in a single dosage. In this manner, compositions of the present invention provide simpler and more convenient dosage regimes. Moreover, as detailed elsewhere herein the compositions of the present invention are believed to provide sustained and controlled release of the active ingredient such that a maximum daily dose of an active ingredient can be administered by single dose without unacceptable "dose-dumping" of the active ingredient such that the active ingredient is steadily administered and provides a therapeutic relief throughout the desired dosing period.

Additional advantages of the gels of the present invention include the overall ease and convenience of administration, including the fact that the gels may be consumed without consuming water and an "on-the-go" dosage form. Furthermore, since the gels are suitable for incorporating high active ingredient loadings, multiple active ingredients may be incorporated into the gels.

Further in accordance with the foregoing, advantageously the gels of the present invention are in a form that provides suitable structural integrity, which provides stability during storage and ease of handling of the gels. Along with this minimum structural integrity/stability, however, the gels are not so rigid that the gels are unbreakable and, therefore, are easily consumed and do not pose a choking risk. Such features are indicated by the preferred ranges of values of various properties highlighted above (e.g., gel strength, Young's modulus, etc.). Furthermore, along with this advantageous balance of structural integrity/breakability, the gels of the present invention combine relatively low syneresis. Accordingly, the features of the gels of the present invention combine to address many issues of conventional gels in a single dosage form.

V. Acetaminophen Gels

One aspect of the present invention is acetaminophen-containing gels including acetaminophen or a pharmaceutically acceptable salt or derivative thereof. Acetaminophen is a commonly-prescribed and used pain reliever. Typically, acetaminophen is administered in capsules or tablets including 250-500 mg per tablet or capsule. The maximum recommended daily dosage of acetaminophen is 4000 mg. Accordingly, if necessary to achieve the maximum recommended daily dosage, a subject is required to consume as many as 8 or more tablets. As noted, the dosage forms of the present invention are suitable for inclusion of large amounts of active ingredient (e.g., loadings of 1 gram or even 2 grams). Accordingly, a single gel of the present invention is equivalent to multiple, conventional acetaminophen capsules or tablets. In fact, a 1 gram (1000 mg) acetaminophen gel is suitable for administering for up to one quarter of the recommended daily dose of 4000 mg while a 2 gram (2000 mg) acetaminophen gel is suitable for administering up to half of the recommended daily dose of 4000 mg. Further advantageously, in combination with the active ingredient loading itself, the gels of the present invention provide sustained delivery of the acetaminophen over suitable periods of time such that administering the greater proportion of the recommended daily dosage does not result in unacceptable "dose dumping" at the outset of delivery of the active ingredient and provides delivery of the acetaminophen over the period of time during which the dosage included in the gel is recommended to be administered. See, for example, Example 2. Accordingly, a particular aspect of the present invention is sustained release acetaminophen gels. Compositions of the present invention are also currently believed to provide sustained delivery of the active ingredient over an administration period of up to 4 hours, up to 8 hours, up to 12 hours, up to 16 hours, up to 20 hours, or even up to 24 hours.

In particular, generally from 50 to 70% of an effective amount of acetaminophen is delivered in from about 0 to about 4 hours after administration, from 60 to 80% of an effective amount of acetaminophen is delivered in from about 4 to about 8 hours after administration, and/or from 80 to 100% of an effective amount of acetaminophen is delivered in from about 8 to about 12 hours after administration.

VI. Methods of Administration and Treatment

The present invention is generally directed to various methods of administration of compositions of the present invention and various methods of treatment of various conditions. For example, the gels of the present invention are suitable for pain treatment of pain, vitamin and mineral supplementation, nutritional supplementation, maintaining and/or improving cardiovascular health, and maintaining and/or improving neurological health. The gels of the present invention may be utilized in accordance with methods known in the art for these and other methods of administration and treatment.

VII. Tamper-Resistant Dosage Form

In addition to the compositions detailed herein, the present invention is also directed to tamper-resistant dosage forms and methods for preventing recovery of active ingredients from a dosage form. Generally, it is currently believed that the compositions of the present invention render it extremely difficult if not nearly impossible to recover certain active ingredients once the active ingredient is included in the compositions. In particular, it is currently believed that when conventional solvent-based recovery processes are attempted in connection with the gels of the present invention that the viscosity of the resulting mixture and the fact that an emulsion is formed make recovery of the active ingredient extremely difficult, if not nearly impossible. Recovery of active ingredients from pharmaceutical dosage forms is often referred to as diversion. Thus, compositions of the present invention may be referred to as tamper-resistant or tamper-proof or diversion-resistant or diversion-proof.

One area where the diversion-resistance nature of the compositions of the present invention is advantageous is in connection with over-the-counter pharmaceutical actives. For example, pseudoephedrine is a widely-used and effective nasal decongestant and is widely regarded as more effective than a proposed substitute, phenylephrine. For years, pseudoephedrine was readily available to consumers as an over-the-counter decongestant. However, in recent years pseudoephedrine has been recovered from over-the-counter medications and utilized to prepare the illegal drug methamphetamine. To combat this diversion of the methamphetamine, some governmental agencies have required a prescription for distribution or sale of pseudoephedrine and/or only permit purchase of a certain amount of pseudoephedrine-containing products over a certain period of time. Advantageously, it has been discovered that commonly-used methods for recovery of pseudoephedrine from over-the-counter medications would not be effective for recovery of the pseudoephedrine from the gel compositions of the present invention, or at the very least would not be effective enough to recovery sufficient quantities of pseudoephedrine for the manufacture of methamphetamine. In this manner, compositions of the present invention including pseudoephedrine could be sold over-the-counter without restriction, but also without the risk of pseudoephedrine diversion for the production of methamphetamine.

VIII. Gastro-Retentive/Sustained Release Dosage Forms

Gastro-retentive dosage forms are known in the art. Generally, gastric-retention refers to retention of a dosage form in the stomach of a patient, or consumer between the cardiac sphincter and the pylorus/pyloric valve. Various mechanisms for gastric retention are known in the art, including, for example, buoyant dosage forms and dosage forms that expand after consumption (e.g., alginate rafts) to a size that prevents passage from the stomach.

Conventional gelling agent-based compositions dissolve in acidic environments after swelling. Accordingly, even though these compositions may swell to a size that could provide gastric retention, their dissolution in acidic conditions encountered in the stomach prevents their utilization as gastric-retentive dosage forms. It has been discovered that incorporating calcium carbonate in the gelling agent-based compositions of the present invention provides a gastric-retentive dosage form. Generally, it has been discovered that inclusion of calcium carbonate prevents dissolution of the composition in an acidic medium. Gastric-retention of a calcium-carbonate-containing composition may be provided via either or both of two mechanisms. As noted, the compositions of the present invention are easily administered and consumed and, in fact, may simply be consumed by swallowing. Due to this ease of administration, relatively large dosage forms may be prepared. Consumption of these dosage forms can be simply swallowing. Once the composition is swallowed, the size of the composition prevents its passage from the stomach through the pyloric sphincter. The composition does not dissolve under the acidic conditions and is thus retained in the stomach. Additionally or alternatively, it has been discovered that the calcium carbonate-containing gelling agent-based compositions of the present invention are buoyant in acidic liquid media for extended periods of time (e.g., up to 24 hours). Thus buoyancy provides retention of the composition in the stomach. During this period of buoyancy, the composition may acquire an outer edge including pockets, or bubbles formed by the release of carbon dioxide from the composition. These pockets are not believed to increase the size of the dosage form, but may to some degree. But regardless of any increase in size of the composition, gastric-retention is provided by the buoyancy of the composition.

Compositions of the present invention are also currently believed to provide sustained delivery of the active ingredient over an administration period of up to 4 hours, up to 8 hours, up to 12 hours, up to 16 hours, up to 20 hours, or even up to 24 hours. In certain embodiments, it is currently believed that sustained release of the active ingredient may, at least in part be provided by calcium carbonate incorporated into compositions of the present invention, the presence of which is believed to contribute to buoyancy of the dosage from and, therefore, sustained release of the active ingredient.

IX. Emulsion Gels

Methods for preparation of gels of the present invention are detailed elsewhere herein, and generally include dispersing one or more active ingredients and other components of the gels (e.g., the gelling agents) throughout an aqueous medium, typically water. These gels may generally be referred to as single-phase gels in which an aqueous phase is constrained within a polymeric matrix formed by the gelling agents by virtue of physical and/or chemical cross-linking between the gelling agents and/or one or more other components of the gels. These single-phase gels have been observed to exhibit one or more advantageous features. For example, these gels have been observed to exhibit advantageous textural properties (e.g., high gel strength to provide structural stability while also providing suitable rupture points to avoid a choking hazard) and low syneresis. Further advantageously, these gels have a relatively high water content which contributes to ease of administration as detailed herein. It is currently believed that the one or more advantageous properties are provided by, for example, the relative proportions of the gelling agents utilized in the gel, the particular gelling agents selected, and/or the water contents of the gel, as detailed above.

Further in accordance with the present invention, gels may be prepared that are in the form of an emulsion (e.g., "emulsion gels"). Such gels are generally prepared by dispersing an oil-based phase (e.g., lipophilic phase) within an aqueous, water-based phase. In particular, dispersing the lipophilic phase within a gelled aqueous phase. In view of the oil-based/lipophilic phase, these gels are suitable for use in connection with lipophilic active ingredients.

In certain embodiments, the present invention is directed to gelling agent-based drug delivery systems for delivery of a lipophilic active ingredient. These active ingredients may include one or more of polyunsaturated fatty acid-containing oils (e.g., fish oils containing omega-3 and omega-6 fatty acids), vitamin oils (e.g., Vitamin E), seed oils (e.g., walnut oil), herb and plant oils (e.g., borage oil, rosemary oil, and evening primrose oil). Thus, in certain such embodiments, the lipophilic active ingredient is selected from the group consisting of omega-3 fatty acids, omega-6 fatty acids, vitamin E, flax seed oil, walnut oil, borage oil, rosemary oil evening primrose oil, and combinations thereof. Often, the lipophilic active ingredient is an omega-3 fatty acid provided by, for example, fish oil or algal oil.

Advantageously, these emulsion gels have been observed to exhibit any and all of the gel characteristics detailed herein, including textural properties such as gel strength, etc. Generally the weight ratio of oil phase to aqueous phase of emulsion gels of the present invention is at least about 0.1:1, at least about 0.2:1, or at least about 0.4:1. Typically, the weight ratio of oil phase to aqueous phase is from about 0.1: to about 0.8:1, or from about 0.25:1 to about 0.8:1. Along with such oil phase to aqueous phase ratios, the water content of the emulsion gels is typically from about 30 wt % to about 60 wt %, or from about 40 wt % to about 50 wt %.

Along with an oil-based phase including the lipophilic active ingredient (e.g., fish oil) and an aqueous phase, these gels include one or more emulsifiers. Suitable emulsifiers include glyercol esters such as glycerol monooleate, sorbitain mono-oleate, polyoxyethylene sorbitan mono-oleate. Suitable emulsifiers also include ethoxylated fatty alcohols such as C6, C7, or C8 polyethoxylates. The one or emulsifiers may also be lecithin or one or more of its components such as phosphatidyl choline. The emulsifiers may also be acetylated mono- or di-glycerides.

Non-limiting examples of suitable emulsifying surfactants include phosphatidyl choline, phosphatidyl serine, phosphatidyl inositol, phosphatidylglycerol, dioleoyl phosphatidylcholine, dioleoylphosphatidylglycerol, dimyristoylphosphatidylcholine, dipalmitoylphosphatidylcholine, phosphatidylethalolamines, phosphatidylserines, sphingomyelins, poly gylcerol esters, ethoxylated castor oils, phospholipids derived from soy, or phospholipids derived from milk-fat globule membrane.

Typically, the one or more emulsifiers constitute from about 0.1 to about 2 wt % of the composition, or from about 0.5 to about 1.5 wt % of the composition, and may be soluble in either the oil-based phase or the aqueous phase.

Certain lipophilic active ingredients, including those listed above, may have a poor taste, or exhibit a poor odor, thereby making their consumption disagreeable, and often undesirable. In certain embodiments, of the present invention, the an emulsion gel includes both a water-soluble flavoring ingredient and a lipophilic flavoring ingredient, with each flavoring ingredient at least reducing, and preferably masking the poor taste or odor provided by the active ingredient (or any other poorly tasting or malodorous component of the lipophilic or aqueous phase). In this manner, certain emulsion gels of the present invention may be referred to as taste-masked emulsion gels.

Various approaches to taste-masking involve coating of active ingredients, including enteric coatings to control release of the active ingredient and thereby avoid a poor taste from consumption of the dosage form. For example, often wax-containing or plastic-containing containing coatings are utilized to provide taste-masking. Advantageously, the taste-masked gels of the present invention do not require such components and, in this manner, may be referred to as "wax-free" or "plastic-free." Further advantageously, the taste-masked gels of the present invention are simply chewable, but avoid the poor and undesirable taste associated with certain active ingredients.

Often, the more basic the gel environment, the more bitter the taste of the gel. Thus, one aspect of the gels of the present invention is including a flavor modifying ingredient that is acidic. Accordingly, one aspect of the emulsion and/or taste-masked gels is incorporating an acidic flavor modifying ingredient selected from the group consisting of malic acid, ascorbic acid, or a combination thereof. Other acidic flavoring agents known in the art are suitable as well.

X. Omega-3 Gel Compositions

In various embodiments, the gels of the present invention include an omega-3 fatty acid. Generally, the omega-3 fatty acid selected from the group consisting of all-cis 7,10,13-hexadecatrienoic acid; all-cis-9,12,15-octadecatrienoic acid (alpha-linolenic acid, ALA); all-cis-6,9,12,15-octadecatetraenoic acid (stearidonic acid); all-cis-8,11,14,17-eicosatetraenoic acid (eicosatetraenoic acid); all-cis-5,8,11,14,17-eicosapentaenoic acid (eicosapentaenoic acid, EPA); all-cis-7,10,13,16,19-docosapentaenoic acid (clupanodonic acid, DPA); all-cis-4,7,10,13,16,19-docosahexaenoic acid (docosahexaenoic acid, DHA); all-cis-4,7,10,13,16,19-docosahexaenoic acid; all-cis-6,9,12,15,18,21-tetracosenoic acid (nisinic acid); and combinations thereof. In various embodiments, the omega-3 fatty acid is selected from the group consisting of ALA, DHA, EPA, DPA, and combinations thereof. In various particular embodiments, the omega-3 fatty acid comprises EPA and DHA.

Typically, the weight ratio of DHA:EPA is from about 95:1 to about 5:1, from about 80:1 to about 20:1, or from about 70:1 to about 30:1. Similarly, the weight ratio of EPA:DHA is from about 95:1 to about 5:1, from about 80:1 to about 20:1, or from about 70:1 to about 30:1.

Generally, the one or more omega-3 fatty acids constitute at least about 5 wt %, at least about 10 wt %, at least 15 wt %, at least about 20 wt %, or at least about 25 wt % of the composition. Typically, the one or more omega-3 fatty acids constitute from about 5 to about 35 wt %, from about 10 to about 35 wt %, or from about 10 to about 20 wt % of the composition.

Omega-3 compositions are known to be suitable for providing health benefits in connection with treatment, prevention, and/or remediation of variety of conditions, including improving cardiovascular health and neurological health.

The source of the omega-3 fatty acid is not narrowly critical and is generally selected from those known in the art, including fish oils, algal oil, squid oil, or plant oils (e.g., echium oil and flaxseed oil). In various embodiments, the source of omega-3 fatty acid is fish oil. In still other embodiments, the source of omega-3 fatty acids is algal oil.

Compositions of the present invention have been identified as suitable for incorporating relatively high proportions of omega-3 fatty acids and, more particularly, proportions of omega-3 fatty acids that are at, near or even higher than the highest loadings of those compositions that are currently commercially available. In some embodiments, the compositions of the present invention contain higher loadings of omega-3 fatty acids than compositions that are currently commercially available.

Generally, gels of the present invention have an omega-3 fatty acid content of at least about 100 mg, at least about 150 mg, at least about 200 mg, at least about 250 mg, at least about 300 mg, at least about 350 mg, at least about 400 mg, at least about 450 mg, at least about 500 mg, at least about 550 mg, at least about 600 mg, at least about 650 mg, at least about 700 mg, at least about 750 mg, at least about 800 mg, at least about 850 mg, at least about 900 mg, at least about 950 mg, or at least about 1000 mg.

Typically, omega-3 gels of the present invention have an omega-3 fatty acid content of from about 100 mg to about 2000 mg, from about 150 mg to about 2000 mg, from about at least about 200 mg to about 1500 mg, from about 250 mg to about 1500 mg, from about 300 mg to about 1500 mg, from about 350 mg to about 1500 mg, from about 400 mg to about 1500 mg, from about 450 mg to about 1500 mg, or from about 500 mg to about 1500 mg.

Further typically, omega-3 gels of the present invention have an omega-3 content of from about 550 mg to about 1250 mg, from about 600 mg to about 1250 mg, from about 650 mg to about 1250 mg, from about 700 mg to about 1250 mg, from about 750 mg to about 1250 mg, from about 800 mg to about 1250 mg, from about 850 mg to about 1250 mg, from about 900 mg to about 1100 mg, from about 950 mg to about 1100 mg, or from about 1000 mg to about 1100 mg.

In still other embodiments, omega-3 gels of the present invention have an omega-3 fatty acid content of at least about 60, at least about 70, at least about 80, at least about 90, at least about 100, at least about 110, at least about 120, at least about 130, at least about 140, at least about 150, at least about 160, at least about 170, at least about 180, at least about 190, or at least about 200 mg omega-3/g composition. Often in accordance with such embodiments, the omega-3 gels have an omega-3 fatty acid content of from about 50 to about 300 mg/g, from about 75 to about 200 mg/g, or from about 100 to about 150 mg omega-3/g composition.

At least one advantage of the high loading of the compositions of the present invention is that a near daily desired dosage or even a full daily desired dosage can be provided by only a single, or a few gel compositions. This is a significant advantage in terms of ease of patient administration and renders the present gels particularly desirable to consumers for delivery of omega-3 fatty acids.

Along with the relatively high omega-3 fatty acid dosage, the present compositions are readily consumed and are not prepared as oversized dosage forms that would be difficult to consume. For example, the omega-3 gels may be in the form and having the dimensions highlighted elsewhere herein.

Additionally or alternatively, the nature, or form of the gel composition is likewise advantageous for delivery of an omega-3 fatty acid. As detailed elsewhere herein, the gels are easily consumed, which may aid in patient compliance generally and more particularly with respect to those patient populations where consuming or swallowing an oral dosage form proves difficult, including the young, the elderly, and patients suffering from dysphagia. Accordingly, the compositions of the present invention may exhibit one or more advantages along with or aside and apart from the fact that high omega-3 content gel compositions are provided.

An advantageous composition may be indicated by one or more rheological properties, in particular, one or more rheological properties that indicate that the gel composition is structurally stable (e.g., has a certain minimum strength), but is also readily broken, or ruptured when consumed or chewed. A variety of such features are identified elsewhere herein, including the appended claims.

For example, in various embodiments, the composition has a Young's modulus (Pa/% strain) of from about 10 to about 95, from about 10 to about 75, from about 10 to about 60, from about 20 to about 50, or from about 25 to about 40.

In these and still other embodiments, the composition has a Young's modulus (Pa/% strain) per unit composition surface area of from about 1 $Pa/cm^2$ to about 10 $Pa/cm^2$, from about 1 $Pa/cm^2$ to about 8 $Pa/cm^2$, or from about 3 $Pa/cm^2$ to about 7 $Pa/cm^2$.

The Young's modulus of compositions of the present invention may be determined by conventional methods known in the art, including the methods detailed herein in the Examples.

The gel strength of the composition may also exhibit an advantageous composition—i.e.—one which is structurally stable to be suitable for processing and storage, but readily consumed, and chewed and broken in the mouth of the consumer. For example, generally the gel strength of the composition per unit composition surface area is from about 0.1 to about 1.75 $kPa/cm^2$, from about 0.25 to about 1.75 $kPa/cm^2$, from about 0.4 to about 1.5 $kPa/cm^2$, or from about 0.6 to about 1.25 $kPa/cm^2$.

Gel strength of the compositions of the present invention may be determined by conventional methods known in the art, including the methods detailed herein in the Examples.

The extensibility of the composition may be from about 50% to about 90%. Additionally or alternatively, the extensibility of the composition may be generally be from about 55% to about 90%, from about 60% to about 85%, or from about 65% to about 75%.

Additionally or alternatively the extensibility of the composition may be from about 1 to about 2%/$m^2$ surface area, from about 1.1 to about 1.8%/$m^2$ surface area, or from about 1.2 to about 1.6%/$m^2$ surface area.

Extensibility of the composition and may be determined by conventional methods known in the art, including those described herein in the Examples.

Another feature is the rupture point of the gels under certain conditions. For example, when a force of from about 0.1 lbs to about 2.2 lbs is applied to the gel composition, the stress-strain curve of the gel composition exhibits a rupture point of from about 90 to about 1000 Pa/%, wherein the rupture point is defined as the ratio of the gel strength (Pa) and the extensibility (%) at the rupture point of the gel.

Along with the structural and rheological properties, the proportions of various components of the omega-3 gels indicate advantageous properties. For example, the gels of the present invention are suitably prepared while having relatively high water content generally, and more specifically a higher water content than conventional, and currently commercially available omega-3 gel compositions. In particular, typically for gels of the present invention—including those exhibiting one or more of the above-noted properties—water constitutes at least about 30 wt %, at least about 40 wt %, at least about 50 wt %, or even at least about 60 wt % of the composition. In addition to the above-noted properties, including the various rheological properties and the relatively high water content, syneresis of the omega-3 gels of the present invention is relatively low. Low syneresis is advantageous as it indicates storage stability and also contributes to maintaining a relatively constant active ingredient loading for a relatively long period of time. For example, generally syneresis of the composition during storage under ambient conditions for 90 days is less than about 10%; less than about 7%, less than about 5%, or less than about 3%.

XI. Bi-Layer Gels

Further in accordance with the present invention, multi-layer gels may be prepared by combining a first gel layer and a second gel layer, with each gel layer generally containing the above-described ingredients and exhibiting one or more of the above-described features (e.g., one or more rheological properties and/or low syneresis). Generally, the multi-layer gels are prepared by combining a first and second gel layer, with the top of surface of a gel layer (e.g., the first gel layer) being in contact with the bottom surface of the other gel layer (e.g., the second gel layer). Generally, the multi-layer gels may include one or more active ingredients, with each gel layer containing the same active ingredient, or each gel layer containing a different active ingredient. In various embodiments, each gel layer of the multi-layer gel includes acetaminophen. Further in accordance with such embodiments, typically one gel layer includes acetaminophen that is coated to provide a release profile different than the acetaminophen contained in the other layer. For example, in various embodiments one layer of the multi-layer gel provides immediate release of the acetaminophen while another layer provides sustained, extended release of the acetaminophen. In accordance with various embodiments, the sustained release acetaminophen layer exhibits one or more of the sustained release properties detailed elsewhere herein for the gels of the present invention.

Having described the invention in detail, it will be apparent that modifications and variations are possible without departing from the scope of the invention defined in the appended claims.

EXAMPLES

The following non-limiting examples are provided to further illustrate the present invention.

Example 1

Konjac/Xanthan Gum/Iota-Carrageenan/Locust Bean Gum

The following example details preparation of a gelling agent-based composition of the present invention. Deionized water (150.0 g) was placed into a 250 ml beaker and stirred with a magnetic stir bar. Calcium chloride (0.30 g) $CaCl_2$, konjac flour (0.15 g), xanthan gum (0.60 g), methyl paraben (0.06 g), and propyl paraben (0.03 g) are then added slowly to the vortex and stirred. At this point the sweeteners, sugars, flavor and coloring agent are added. After all excipients are completely dispersed the stir bar is removed and the overhead mixer equipped with a 1.5" 3 blade impeller is used to mix at 550 rpm. The beaker is covered and the solution is heated to approximately 85-90° C. using a hot plate. Once the temperature is reached the mixing rate is increased to 800 rpm and the iota-carrageenan (0.40 g) and locust bean gum (0.40 g) are added slowly to the vortex. The solution is then stirred until all components are completely dispersed.

Table 1 sets forth formulation details for two compositions prepared in accordance with the above method. Formula 8411-A was prepared including konjac flour as detailed above. A second formulation 72911-C was prepared without addition of konjac four. As shown in the syneresis testing results below, inclusion of konjac flour contributes to lower syneresis.

TABLE 1

| Reagent | Mass (g) 72911-C | Mass (g) 8411-A | Supplier* |
|---|---|---|---|
| DI $H_2O$ | 150.0 | 150.0 | PDI |
| $CaCl_2$ | 0.30 | 0.30 | n/a; $[Ca^{2+}]$ = 324 ppm |
| Konjac Flour | 0.00 | 0.15 | FMC Biopolymer (Nutricol Gp 312) |
| Xanthan Gum | 0.60 | 0.60 | CP Kelco |
| Iota-Carrageenan | 0.40 | 0.40 | Tic Gums |
| Locust Bean Gum | 0.40 | 0.40 | Tic Gums |
| Methyl Paraben | 0.06 | 0.06 | n/a |
| Propyl Paraben | 0.03 | 0.03 | n/a |

Samples of each composition were subjected to texture analysis utilizing a TA XT Express texture analyzer under the following conditions:
Stress-Strain Curve
Sample Shape: cylinder
Sample Dimensions: 22 mm (width)×17 mm (height)
Instrument: TA XT Express Texture Analyzer
Probe: 1" diameter cylinder derlin radiused
Test Type: 2 cycle compression texture profile analysis
Distance: 10 mm
Pre-Test Speed: 1 mm/sec
Test Speed: 0.8 mm/sec
Post Test Speed: 1 mm/sec Following are the results for Gel Strength and Extensibility measured at the rupture point (peak maximum) of the sample's stress-strain curve.

|  | 72911-C | 8411-A |
|---|---|---|
| Gel Strength (kPa): | 24.504 | 36.79 |
| Extensibility (%): | 69.257 | 71.484 |

Each of the above-described samples was also tested to determine the amount and rate of syneresis, during storage. Each sample was placed in a sealed MYLAR bag and stored at room temperature (approx. 25° C.). After a pre-determined amount of time the bag was opened and the sampled was removed. Any water in the MYLAR bag was recovered using an absorbent towel and the mass of the water was determined. Following are the results for the first testing interval.

| Batch # | Mass of Sample | # Days Sealed in Mylar Bag | Mass of $H_2O$ | % $H_2O$ Loss |
|---|---|---|---|---|
| 72911-C | 3.74 g | 8 | 0.76 g | 2.0% |
| 8411-A | 5.65 g | 7 | 0.04 g | 0.7% |

The samples were then resealed in their MYLAR pouches and stored at room temperature for a second period of time and after four days they were opened and the water was observed.

| Batch # | Mass of Sample | # Days Sealed in Mylar Bag | Mass $H_2O$ | % $H_2O$ Loss |
|---|---|---|---|---|
| 72911-C | 2.82 g | 4 | 0.04 g | 1.4% |
| 8411-A | 5.57 g | 4 | 0.00 g** | 0.00% |

**The amount of water loss was negligible relative to the precision of the balance (balance precision: ±0.01 g)

Example 2

Konjac/Xanthan Gum/Locust Bean Gum

The following example details preparation of gelling agent-based compositions including konjac, xanthan gum, and locust bean gum.

Deionized water (147.0 g) is weighed out into a 250 ml beaker. Sodium citrate (1.50 g) is added and stirred with a stir bar until dissolved. Sucralose and xylitol (0.2940 g, 0.2% w/w) each are weighed out and added to the solution. Konjac powder (0.30 g) is then weighed out and slowly added to the vortex then allowed to dissolve over approximately 5 minutes. At this point the stir bar is removed and the overhead mixer is equipped with a 1.5" 3 blade impeller and used to stir the solution at 250 rpm while heating the solution to 85° C. Once the solution has reached 85° C., xanthan gum (0.75 g) is added very slowly over the course of 30 seconds and the resulting mixture is stirred for approximately 20 minutes. Once the xanthan gum is well dispersed, the mixing rate is increased to 550 rpm and locust bean gum (0.30 g) is added under high shear and the mixture is mixed for approximately 20 minutes. Methyl paraben (0.0600 g) and propyl paraben (0.0300 g) are then added and stirred for an additional 5 minutes.

For incorporation of an active ingredient an appropriate amount of blank gel is then weighed out and placed into a clean 250 ml beaker and the desired active ingredient is slowly added and the mixture is stirred for approximately 20 minutes. The gel is then poured into the desired dosage form and stored for further use.

Texture Analysis

Blank gel samples (40-50 ml) were poured into a 50 ml beaker (bloom jar) and covered. The samples were allowed to set in a refrigerator or at room temperature (approximately 25° C.) for at least an hour before use. A TA XT Express texture analyzer equipped with a 0.5" diameter cylinder delrin radiused probe having a contact area of 126.68 $mm^2$ was utilized for the testing. Gel strength was determined using the "BS757 Gelatine Bloom" project preprogrammed in the Exponent Lite software with a data acquisition rate of 200 points per second (pps) and a penetration depth of 4 mm. The following table provides results of testing for blank gels (placebo), gels in which 25 wt. % calcium carbonate were incorporated, and gels in which 10 wt. % fish oil is incorporated.

| Gel | Force (g) | Stress (kPa) | # of tests | Notes |
| --- | --- | --- | --- | --- |
| 25% $CaCO_3$ | 24.7 | 1.906 | 4 | Conditioned at room temperature |
| 25% $CaCO_3$ | 22.3 | 1.724 | 4 | Conditioned at room temperature |
| 25% $CaCO_3$ | 61.8 | 4.784 | 1 | Conditioned in the fridge |
| 15% $CaCO_3$ | 21.6 | 1.672 | 3 | n/a |
| Placebo | 25.5 | 1.976 | 4 | Conditioned at room temperature |
| Placebo | 23.6 | 1.831 | 3 | Conditioned at room temperature |
| Placebo | 26.0 | 2.011 | 2 | Conditioned in the fridge and stored at room temperature for 1 hour before analysis. |
| Placebo | 22.4 | 1.737 | 2 | Conditioned at room temperature |
| 10% Fish oil | 28.1 | 2.175 | 3 | No locust bean gum |
| 10% Fish oil | 30.9 | 2.392 | 3 | With locust bean gum |

Syneresis Testing 6 gels samples were made following the above method: 4 blank gels and 2 gels including 15 wt % $CaCO_3$. The gels were then stored at room temperature in aluminum foil lined TUPPERWARE containers. For analysis, the gels were removed and weighed before returning the gels to the container to determine water loss. The aluminum foil on which the gel samples rested was dabbed with an absorbent towel to rid the container of any water.

| Conditioned | | day 0 | 3 days | 4 days | 6 days | Total Loss (g) |
| --- | --- | --- | --- | --- | --- | --- |
| Blank Gel | | | | | | |
| room temp | 1 | 8.97 g | 8.88 g | 8.85 g | 8.80 g | 0.17 |
| room temp | 2 | 9.14 g | 9.04 g | 9.01 g | 8.97 g | 0.17 |
| Fridge | 3 | 11.20 g | 11.17 g | 11.12 g | 11.08 g | 0.12 |
| Fridge | 4 | 10.86 g | 10.79 g | 10.75 g | 10.70 g | 0.16 |
| 15% CaCO3 | | | | | | |
| room temp | 1 | 9.04 g | 8.91 g | 8.86 g | 8.77 g | 0.27 |
| Fridge | 2 | 11.03 g | 10.92 g | 10.86 g | 10.78 g | 0.25 |

Dissolution Kinetics

Following are the results of dissolution testing for gels prepared incorporating niacin or acetaminophen as active ingredients.

A stock solution of niacin was prepared by weighing nicotinic acid (0.1000 g) into a 100 ml volumetric flask that was filled with deionized water (pH 1.496) (1 mg/ml). The solution was then stirred until the nicotinic acid was dissolved. From the stock solution, three standard solutions were prepared via serial dilution: 1 ml of the stock solution was diluted to 50 ml with pH 1.496 DI $H_2O$: 20.00 µg/ml; 5 ml of the 20.00 µg/ml solution was diluted to 50 ml with pH 1.496 DI $H_2O$: 2.000 µg/ml; 2 ml of the 2.000 µg/ml solution was diluted to 10 ml with pH 1.496 DI $H_2O$: 0.4000 µg/ml.

The standard solutions were analyzed using a Cary 50 UV-Vis absorption spectrophotometer operated at 262.0 nm. DI $H_2O$ (pH 1.496) was used as the blank before each reading. 3 readings were taken and averaged for each standard solution. The averages of the absorption readings (ordinate) were plotted against their respective concentrations (absicca) and a linear regression was fit to the points. The results are shown in FIG. 1.

To determine the rate of release of niacin from gel compositions of the present invention, gels were prepared including nicotinic acid as the active ingredient, both with and without calcium carbonate as an additional excipient.

Nicotinic acid/calcium carbonate-containing gels were made in accordance with the above method. $CaCO_3$ (10%) 9.80 g was dissolved into 98.05 g of blank gel and stirred for 20 minutes. Approximately 10 g doses were poured into a boat-shaped mold and used as the blank for the dissolution analysis (03292011-A). Nicotinic acid (1.60 g) nicotinic acid was added to the remaining 64.23 g of $CaCO_3$-containing gel and stirred for approximately 20 minutes. Approximately 10 g doses were poured into a boat-shaped mold for dissolution analysis (03292011-B).

Nicotinic acid-containing gels without calcium carbonate were also prepared in accordance with the above method. Prior to the addition of nicotinic acid as the active ingredient, approximately 10 g doses of the gel were poured out into a boat-shaped mold and used as the blank for dissolution analysis (03302011-A). Nicotinic acid (1.51 g) (2.5%) was added to 60.54 g of blank gel and stirred for 20 minutes. Approximately 10 g doses of nicotinic acid-containing gel were poured out into a boat-shaped mold and used for dissolution analysis (03302011-B).

Following are the conditions of the dissolution analysis. Generally, the approximately 10 g samples were placed in a water bath heated above room temperature and the bath was agitated to determine the dissolution kinetics of the nicotinic acid active ingredient.

Experimental conditions for the dissolution of niacin gel containing $CaCO_3$.

| Bath: | 1000 ml, pH 1.502 DI $H_2O$ |
| --- | --- |
| Temperature: | 37° C. ± 1 |
| Mixing Type: | Paddle |
| Mixing Rate: | 75 rpm |
| Detector: | UV-Vis; 262.0 nm |

| Gel | % API/% excipient | Mass (g) |
| --- | --- | --- |
| Sample: | 2.5% niacin/10% $CaCO_3$ | 9.50 |
| Blank: | none/10% $CaCO_3$ | 9.50 |

Experimental conditions for the dissolution of niacin gel.

| Bath: | 1000 ml, pH 1.50 DI $H_2O$ |
| --- | --- |
| Temperature: | 37° C. ± 1 |
| Mixing Type: | Paddle |
| Mixing Rate: | 75 rpm |
| Detector: | UV-Vis; 262.0 nm |

| Gel | % API | Mass (g) |
| --- | --- | --- |
| Sample: | 2.5% niacin | 9.20 |
| Blank: | none | 9.30 |

Figure 2:
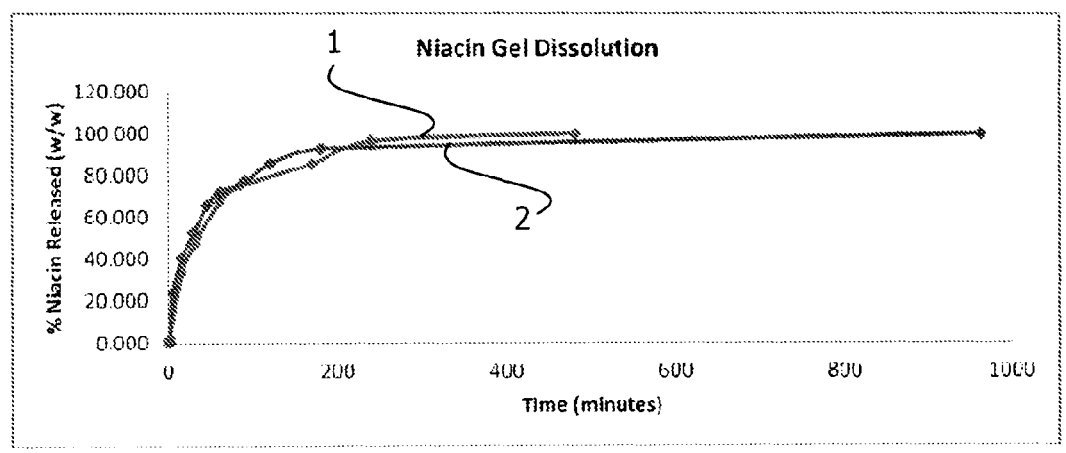

FIG. 2 depicts the dissolution profiles for the niacin gels in terms of % niacin released over time.

Curve 1: % Niacin released over an 8 hour period. 9.5 g sample containing 2.5% nicotinic acid and 10% $CaCO_3$. A placebo containing 10% $CaCO_3$ was used as the blank.

Curve 2: % Niacin released over a 16 hour period. 9.20 g sample containing 2.5% nicotinic acid. A placebo was used as the blank.

Acetaminophen-containing gels were also prepared to determine the release kinetics of acetaminophen. A stock acetaminophen-containing solution was prepared. Acetaminophen (0.1002 g) was weighed out into a 100 ml volumetric flask and filled to the line with deionized water (pH 1.5). The mixture was then stirred until the acetaminophen was completely dissolved. Standard solutions were prepared via serial dilution of the stock solution: 1 ml of the above stock solution was diluted to 50 ml with pH 1.50 deionized (DI) $H_2O$: 20.04 µg/ml; 5 ml of the 20.04 µg/ml solution was diluted to 50 ml with pH 1.50 DI H$_2$O: 2.004 µg/ml; and 2 ml of the 2.004 µg/ml solution was diluted to 10 ml with pH 1.50 DI H$_2$O: 0.4008 µg/ml.

Figure 3:
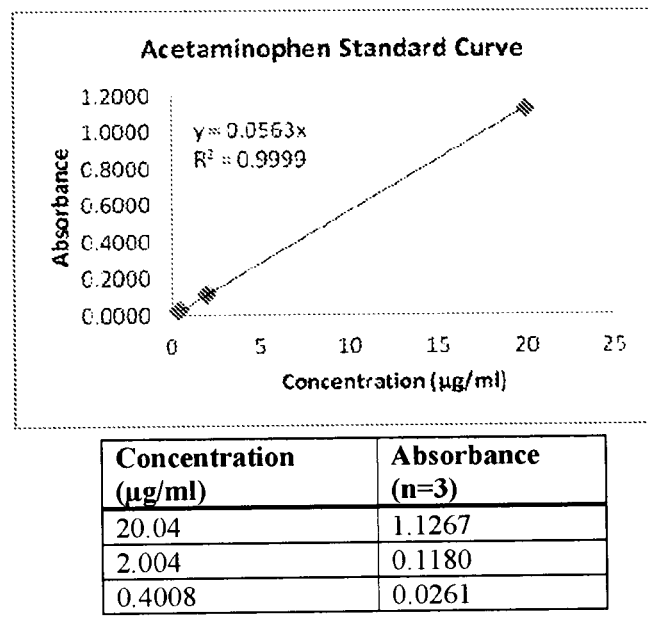
FIGS. 3 and 4 provide the results of acetaminophen dissolution testing described in Example 2.

The standard acetaminophen solutions were analyzed using a Cary 50 UV-Vis absorption spectrophotometer operated at 250.0 nm. DI H$_2$O (pH 1.50) was used as the blank before each reading. 3 readings were taken and averaged for each standard solution. The results are shown in FIG. 3. The averages of the absorption readings (ordinate) were plotted against their respective concentrations (absicca) and a linear regression was fit to the points. The concentration is based on standard solutions with their respective absorbance readings. For the acetaminophen standard curve $\epsilon=8535.64$ M$^{-1}$ cm$^{-1}$; the slope of the linear regression was determined to be 0.0563 ml µg$^{-1}$ cm$^{-1}$.

To determine the rate of release of acetaminophen from gel compositions of the present invention, gels were prepared in accordance with the above description both with and without calcium carbonate as an additional excipient. Acetaminophen (5.72 g) (6.5%) was added to 88.05 g of blank gel and stirred for approximately 20 minutes. CaCO$_3$ (6.06 g) (10%) was added to 60.60 g of the acetaminophen gel and stirred for approximately 20 minutes. Approximately 10 g doses were poured into a boat-shaped mold and used for dissolution analysis (03302011-D). For acetaminophen gels without CaCO$_3$, acetaminophen (5.72 g) (6.5%) was added to 88.05 g of blank gel and stirred for approximately 20 minutes. Approximately 10 g doses were poured out into a boat-shaped mold and used for dissolution analysis (03302011-C).

Dissolution analysis was conducted as generally described above in connection with niacin gels and under the following conditions.

Experimental conditions for the dissolution of acetaminophen gel containing CaCO$_3$.

| Bath: | 1000 ml, pH 1.49 DI H$_2$O |
|---|---|
| Temperature: | 37° C. ± 1 |
| Mixing Type: | Paddle |
| Mixing Rate: | 75 rpm |
| Detector: | UV-Vis; 250.0 nm |

| Gel | % API/% Excipient | Mass (g) |
|---|---|---|
| Sample: | 6.5% acetaminophen/10% CaCO$_3$ | 9.49 |
| Blank: | none/10% CaCO$_3$ | 9.61 |

Experimental conditions for the dissolution of acetaminophen gel.

| Bath: | 1000 ml, pH 1.50 DI H$_2$O |
|---|---|
| Temperature: | 37° C. ± 1 |
| Mixing Type: | Paddle |
| Mixing Rate: | 75 rpm |
| Detector: | UV-Vis; 250.0 nm |

| Gel | % API | Mass (g) |
|---|---|---|
| Sample: | 6.5% acetaminophen | 9.78 |
| Blank: | none | 9.63 |

Figure 4:
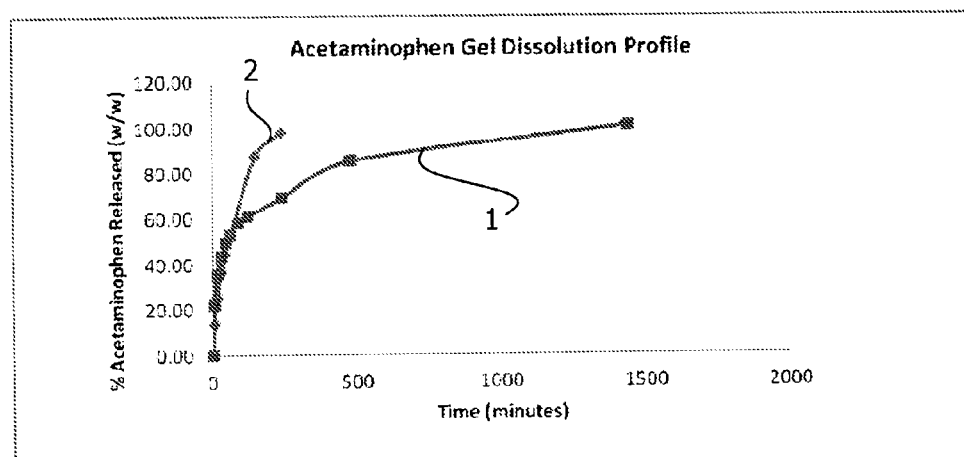

FIG. 4 depicts the dissolution profiles for the acetaminophen gels in terms of % acetaminophen released over time.

Curve 1: % Acetaminophen released over a 24 hour period. 9.49 g sample consisting of 6.5% acetaminophen and 10% CaCO$_3$. A placebo containing 10% CaCO$_3$ was used as the blank.

Curve 2: % Acetaminophen releases over a 4 hour period. 9.78 g sample containing 6.5% acetaminophen. A placebo was used as the blank.

Model Esophagus Testing

To determine the ease of administration of compositions of the present invention, a model esophagus was constructed and compositions were passed therethrough under various conditions. 70.6 cm of 33 mm clear collagen sausage casing coated with different materials was fixed to PVC pipe split lengthwise in half. The PVC pipe was attached to a stand and adjusted to 60° relative to horizontal. Video recording was obtained from a bird's eye position. The gel dosage (boat-shaped form) was placed inside the sausage casing then water was poured down the back to propel the gel downwards. The amount of water needed to propel the gel to the end was measured.

Experimental conditions and results for the model esophagus.

| Video # | 1 | 2 | 3 | 4 | 5 |
|---|---|---|---|---|---|
| Coating: | None | H$_2$O | Mineral oil | Surgilube | Surgilube |
| Volume of Water (ml): | 34.7 | 9.42 | 3.16 | 20.57 | 23.06 |
| Notes: | — | — | — | — | Gel was coated with surgilube |

Example 3

Gellan Gum/Xanthan Gum/Locust Bean Gum

The following example details preparation and testing of gelling agent-based compositions of the present invention.

Sodium citrate (1.0 g), xylitol (0.30 g), and sucralose (0.30 g) were dissolved in deionized water (150.0 g) using a magnetic stir bar. The gellan gum (0.30 g) is added and the mixture is stirred until the gellan gum is completely dispersed. The magnetic stir bar is removed and an overhead mixer equipped with a 1.5" 3 blade impeller is used to mix the solution at 350 rpm. Xanthan gum (0.60 g) is added and stirring is continued until all components are completely dispersed. The beaker is then covered and the solution is heated to approximately 85-90° C. After heating, methyl paraben (0.06 g) and propyl paraben (0.03 g) are added. Mixing is then continued at an increased rate of 650 rpm and locust bean gum (0.06 g) is added slowly. The solution is then stirred for another 20 minutes.

The compositions of the formulations of the current example incorporate a source of sodium ions. This component is currently believed to impact the brittleness, or rupture point of the gels. To determine the impact of the source of sodium ions on the brittleness and other rheological properties of these gels they were subjected to analysis utilizing the TA XT Express texture analyzer described above. For this analysis, a sample of a blank gel was poured into a 22 mm diameter by 12 mm high mold and allowed to cool. The stress strain curve for the samples was then determined.

Texture analysis was conducted under the following conditions. The results are provided in the stress-strain curve and Table appearing below.

| T.A. Sequence: | Return to Start |
|---|---|
| Test Mode: | Compression |
| Test Speed: | 0.8 mm/sec |

-continued

| | |
|---|---|
| Distance: | 10 mm |
| Probe: | ½" diameter cylinder derlin radiused |
| Stress Area (area of probe): | 126.68 mm² |
| Data Acquisition: | 400 points per sec |

Figure 5A:
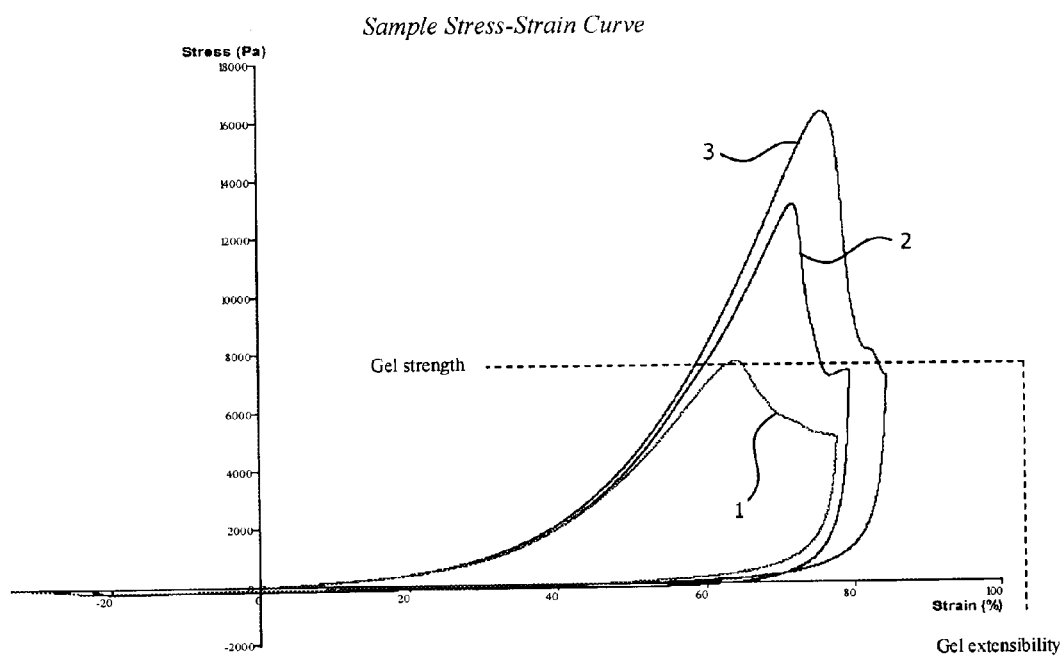
FIGS. 5A and 5B are stress-strain curves for texture analysis conducted as described in Example 3.
Figure 5B:
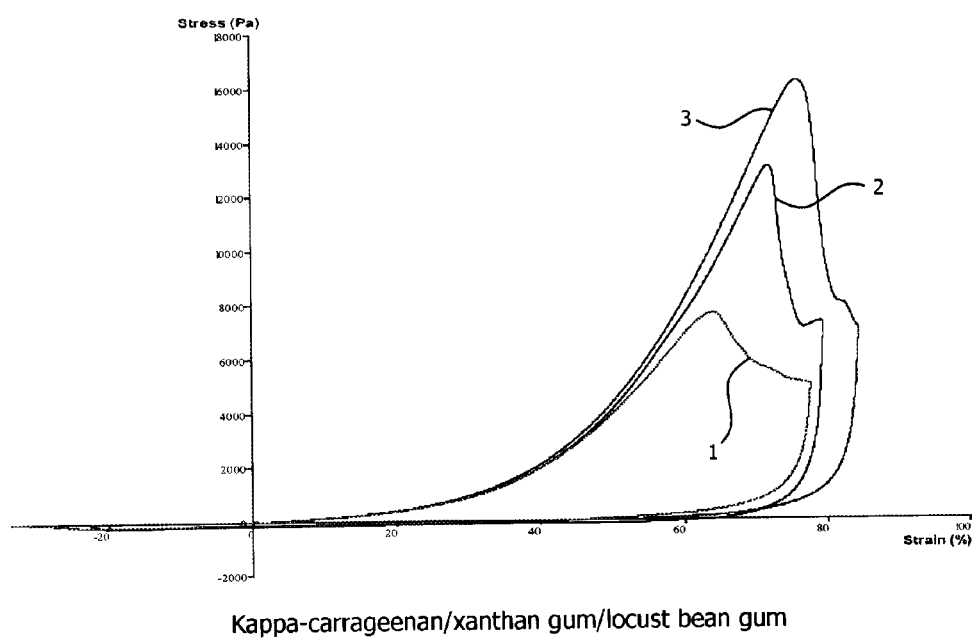

FIGS. 5A and 5B are sample stress-strain curve.

The following Tables provide details of the compositions prepared and results of texture analysis.

| Batch # | Water (g) | Gellan (g) | Locust Bean Gum (g) | Xanthan Gum (g) | Sodium Citrate (g) |
|---|---|---|---|---|---|
| 52711-A | 150 | 0.7 | 0.45 | 0.45 | 0.0725 |
| 53111-A | 150 | 0.9 | 0.45 | 0.45 | 0.9 |
| 53111-B | 150 | 0.225 | 0.45 | 0.45 | 0.0725 |
| 53111-C | 150 | 0.225 | 0.45 | 0.9 | 0.0725 |
| 60111-A | 150 | 0.45 | 0.45 | 0.45 | 0.2175 |
| 60111-B | 150 | 0.9 | 0.225 | 0.225 | 0.45 |
| 60111-C | 150 | 0.45 | 0.225 | 0.675 | 0.45 |
| 60211-P | 150 | 0.5 | 0.3 | 0.7 | 0.5 |
| 60311-A | 150 | 0.3 | 0.3 | 0.75 | 0.45 |
| 60311-B | 150 | 0.15 | 0.45 | 0.75 | 0.45 |
| 60311-C | 150 | 0.3 | 0.3 | 0.75 | 0.9 |
| 60311-R | 150 | 0.5 | 0.5 | 0.5 | 0.5 |
| 60611-A | 150 | 0.3 | 0.525 | 0.525 | 0.9 |
| 60711-A | 150 | 0.3 | 0.525 | 0.525 | 0.45 |
| 60711-B | 150 | 0.3 | 0.3 | 0.3 | 0.45 |
| 60711-C | 150 | 0.3 | 0.45 | 0.3 | 0.45 |
| 60811-A | 150 | 0.3 | 0.45 | 0.2 | 0.45 |
| 60811-B | 150 | 0.3 | 0.6 | 0.2 | 0.45 |
| 60811-C | 150 | 0.3 | 0.6 | 0.3 | 0.45 |
| 60811-D | 150 | 0.2 | 0.6 | 0.3 | 0.45 |
| 60811-E | 150 | 0.4 | 0.6 | 0.3 | 0.45 |
| 61411-A | 150 | 0.3 | 0.6 | 0.3 | 0.3 |
| 61411-B | 150 | 0.3 | 0.6 | 0.3 | 0.6 |
| 61411-D | 150 | 0.3 | 0.6 | 0.2 | 0.6 |
| 61411-E | 150 | 0.2 | 0.6 | 0.3 | 0.6 |
| 61511-A | 150 | 0.2 | 0.6 | 0.3 | 0.6 |
| 61511-B | 150 | 0.2 | 0.6 | 0.3 | 0.6 |
| 61611-C | 150 | 0.3 | 0.6 | 0.3 | 0.45 |
| 61711-A | 150 | 0.3 | 0.6 | 0.3 | 0.40 |
| 61711-B | 150 | 0.3 | 0.6 | 0.3 | 0.31 |
| 61011-B | 150 | 0.2 | 0.6 | 0.3 | 0.45 |
| 61011-A | 150 | 0.2 | 0.6 | 0.3 | 0.45 |

| Batch # | Extensibility (%) | Strength (Pa) | Rupture Point (Pa/%) | Note |
|---|---|---|---|---|
| 52711-A | 49.07 | 4813 | 98.08 | |
| 53111-A | 62.46 | 5120 | 81.97 | |
| 53111-B | 83.92 | 16722 | 199.27 | |
| 53111-C | 96.6 | 54765 | 566.95 | |
| 60111-A | 69.79 | 14111 | 202.19 | |
| 60111-B | 52.93 | 909 | 17.17 | |
| 60111-C | 67.34 | 10917 | 162.12 | |
| 60211-P | 63.83 | 10783 | 168.95 | |
| 60311-A | 69.17 | 17911 | 258.94 | |
| 60311-B | 70.96 | 31280 | 440.81 | |
| 60311-C | 70.09 | 20979 | 299.32 | |
| 60311-R | 61.16 | 13787 | 225.43 | |
| 60611-A | 73.17 | 28637 | 391.37 | |
| 60711-A | 74.34 | 30333 | 408.02 | |
| 60711-B | 69.35 | 8918 | 128.59 | |
| 60711-C | 67.41 | 10937 | 162.24 | |
| 60811-A | 69.53 | 8344 | 120 | |
| 60811-B | 70.99 | 6495 | 91.5 | |
| 60811-C | 69.02 | 13313 | 192.88 | |
| 60811-D | 71.55 | 11460 | 160.17 | |
| 60811-E | 67.35 | 7257 | 107.75 | |
| 61411-A | 72.84 | 13765 | 188.98 | |
| 61411-B | 71.91 | 14027 | 195.06 | |
| 61411-D | 69.25 | 5394 | 77.9 | |
| 61411-E | 71.78 | 15368 | 214.1 | |
| 61511-A | 72.49 | 33741 | 465.44 | 10% CaCO₃ |
| 61511-B | 75.21 | 26597 | 353.63 | 25% CaCO₃ |
| 61611-C | 56.77 | 14786 | 260.45 | NaCl |
| 61711-A | 59.77 | 14548 | 243.42 | KCl |
| 61711-B | 67.37 | 9047 | 134.29 | NaCl |
| 61011-B | 64.34 | 7685 | 119.44 | 1.5 g Pullulan |
| 61011-A | 75.96 | 16309 | 214.71 | 3.0 g Pullulan |

Samples of varying compositions were also tested to determine syneresis, during storage for various times. Gel samples (approx. 5 g) were poured into a circular mold having a volume of approx. 6.7 cm³ to provide compositions having a surface area of approx. 20 cm² and allowed to cool. Each sample was then weighed and placed on a plastic tray in a ZIPLOC bag for storage. Gel samples were weighed at different daily intervals and the plastic tray was dried of any water with an absorbent towel. The percent loss was determined by the equation: % loss=100*[(initial mass−current mass)/initial mass].

Syneresis Analysis
Mass (g)

| Batch # | Jun. 8, 2011 | Jun. 10, 2011 | Jun. 13, 2011 | Jun. 14, 2011 | Jun. 15, 2011 | Jun. 16, 2011 | Jun. 17, 2011 | % Loss | # Days | % Loss/day | Notes |
|---|---|---|---|---|---|---|---|---|---|---|---|
| 60711-C | 3.07 | 2.89 | 2.62 | 2.52 | 2.44 | 2.35 | 2.25 | 26.71 | 9.00 | 2.97 | |
| 60811-A | 3.19 | 3.00 | 2.72 | 2.62 | 2.55 | 2.44 | 2.34 | 26.65 | 9.00 | 2.96 | |
| 60811-B | 3.34 | 3.18 | 2.91 | 2.80 | 2.72 | 2.63 | 2.53 | 24.25 | 9.00 | 2.69 | |
| 60811-C | 3.24 | 3.04 | 2.76 | 2.66 | 2.58 | 2.47 | 2.38 | 26.54 | 9.00 | 2.95 | |
| 60811-D | 3.68 | 3.47 | 3.20 | 3.11 | 3.01 | 2.91 | 2.80 | 23.91 | 9.00 | 2.66 | |
| 60811-E | 3.17 | 2.96 | 2.69 | 2.58 | 2.50 | 2.41 | 2.32 | 26.81 | 9.00 | 2.98 | |
| 61011-A | n/a | 3.06 | 2.70 | 2.63 | 2.58 | 2.52 | 2.44 | 20.26 | 7.00 | 2.89 | |
| 61011-B | n/a | 3.52 | 3.19 | 3.13 | 3.08 | 3.01 | 2.95 | 16.19 | 7.00 | 2.31 | |
| 61411-A | n/a | n/a | n/a | 2.91 | 2.83 | 2.76 | 2.69 | 7.56 | 3.00 | 2.52 | |
| 61411-B | n/a | n/a | n/a | 3.35 | 3.26 | 3.19 | 3.13 | 6.57 | 3.00 | 2.19 | |
| 61411-D | n/a | n/a | n/a | 3.01 | 2.95 | 2.88 | 2.77 | 7.97 | 3.00 | 2.66 | |
| 61411-E | n/a | n/a | n/a | n/a | 3.24 | 3.15 | 3.04 | 6.17 | 2.00 | 3.09 | |
| 61511-A | n/a | n/a | n/a | n/a | 3.64 | 3.56 | 3.49 | 4.12 | 2.00 | 2.06 | 10% CaCO₃ |
| 61511-B | n/a | n/a | n/a | n/a | 3.39 | 3.32 | 3.25 | 4.13 | 2.00 | 2.06 | 25% CaCO₃ |
| 61611-C | n/a | n/a | n/a | n/a | n/a | 3.04 | 2.97 | 2.30 | 1 | 2.30 | NaCl |
| 61711-A | n/a | n/a | n/a | n/a | n/a | n/a | 3.59 | | | | KCl |
| 61711-B | n/a | n/a | n/a | n/a | n/a | n/a | 2.74 | | | | NaCl |

Example 4

This example details comparative texture analysis testing of gellan gum-containing gels prepared in accordance with Example 3 and gel compositions prepared that included Gelcarin DG 654B (a mixture of kappa-carrageenan, locust bean gum and potassium citrate).

The Gelcarin formulations were prepared by the following procedure. Potassium chloride in an amount suitable to provide the desired final gel content was dissolved in deionized water in a 250 ml beaker. An overhead mixer equipped with a 1.5" 3 blade impeller is then used to mix the solution at 350 rpm. While cold, Gelcarin DG 654B and xanthan gum (and optionally pullulan in an amount suitable to provide the desired content pullulan content) were slowly added and stirred until completely dispersed. The beaker is then covered and the mixing rate increased to 500 rpm and the solution is heated to 85-90° C. Once the target temperature is reached, locust bean gum is added slowly and the mixing rate is increased to 600 rpm. The solution is stirred for 20 minutes. Methyl paraben and propyl paraben are added to provide the prescribed compositions are added in the appropriate amount.

Gelcarin-containing compositions of the following formulations were prepared and subjected to texture analysis in accordance with the conditions set forth above.

| Batch # | Gelcarin 654B | Xanthan Gum | Pullulan | Locust Bean Gum | KCl | Gel Strength (Pa) |
|---|---|---|---|---|---|---|
| 62811-A | 0.45 | 0.9 | 3 | 0.45 | 0.075 | 59721 |
| 62811-B | 0.45 | 0.9 | 1.5 | 0.45 | 0.075 | 54884 |
| 62811-C | 0.45 | 0.9 | 0 | 0.45 | 0.075 | 61561 |
| 62811-D | 0.45 | 0.75 | 0 | 0.45 | 0.075 | 19996 |
| 62811-E | 0.45 | 0.6 | 0 | 0.45 | 0.075 | 31600 |
| 62811-F | 0.45 | 0.75 | 1.5 | 0.45 | 0.075 | n/a |
| 62811-G | 0.45 | 0.75 | 1.5 | 0.45 | 0.15 | 73906 |
| 63011-A | 0.45 | 0.6 | 1.5 | 0.45 | 0.15 | 61496 |
| 63011-B | 0.45 | 0.6 | 1.5 | 0.45 | 0.23 | 49246 |
| 7111-A | 0.45 | 0.6 | 1.5 | 0.45 | 0.5 | 70694 |
| 7111-B | 0.45 | 0.6 | 1.5 | 0.6 | 0.075 | 48603 |
| 7111-C | 0.45 | 0.45 | 1.5 | 0.45 | 0.075 | 25425 |
| 7511-A | 0.45 | 0.6 | 1.5 | 0.45 | 0.075 | 33563 |
| 7511-B | 0.6 | 0.6 | 1.5 | 0.45 | 0.075 | 38273 |
| 7511-C | 0.45 | 0.6 | 1.5 | 0.45 | 1 | 55606 |
| 7511-D | 0.45 | 0.6 | 0.5 | 0.45 | 0.075 | 49113 |
| 7511-E | 0.45 | 0.6 | 1.5 | 0.45 | 0.075 | 18146 |
| 7611-A | 0.45 | 0.6 | 0.75 | 0.45 | 0.075 | 43109 |
| 7611-B | 0.45 | 0.6 | 1.5 | 0.2 | 0.075 | 41932 |
| 7611-C | 0.45 | 0 | 1.5 | 0.45 | 0.075 | 8761 |
| 7611-D | 0.45 | 0.6 | 1.5 | 0.45 | 0 | 23271 |
| 7611-E | 0.45 | 0.5 | 0.5 | 0.45 | 0.03 | 28805 |
| 7711-A | 0.45 | 0.6 | 0.5 | 0.45 | 0 | 17449 |
| 7711-B | 0.45 | 0.5 | 0.5 | 0 | 0.03 | 10201 |
| 7711-C | 0.45 | 0.5 | 0.5 | 0.6 | 0.01 | 23356 |
| 7711-D | 0 | 0.5 | 0.5 | 0.45 | 0.03 | 20924 |

Following are the texture analysis results for the gellan-containing formulations and the Gelcarin-containing formulations.

| Batch # | Hardness (lbs) | Modulus (lbs/in$^2$) | Brittleness (%) |
|---|---|---|---|
| 62811-A | 2.0536 | 0.8138 | 77.38 |
| 62811-C | 1.7532 | 0.5082 | 79.58 |
| 7611-C | 0.2495 | 0.3219 | 73.27 |
| 7611-D | 0.6627 | 0.3587 | 74.36 |
| 7611-E | 0.8203 | 0.3775 | 75.93 |
| 7711-B | 0.2905 | 0.2046 | 73.53 |
| 60111-A | 0.1823 | 0.3874 | 69.79 |
| 60311-C | 0.5617 | 0.3259 | 68.85 |
| 60611-A | 0.7838 | 0.3217 | 72.77 |
| 60711-A | 0.8638 | 0.4170 | 74.34 |
| 60811-C | 0.3791 | 0.2553 | 69.02 |
| 61411-E | 0.4377 | 0.2301 | 71.78 |

Kappa-Carrageenan/Xanthan Gum/Locust Bean Gum

Example 5

This example details preparation and testing of compositions of the present invention including kappa-carrageenan, xanthan gum, locust bean gum and, optionally, a source of potassium ions. As shown below, the rheological properties of these gels are controlled to provide strength to the gel, yet the gel will rupture in a very controlled manner. Also, extensibility is controlled such that breakage is controlled to a break in the event that a blockage occurs.

Below are the results of syneresis testing, texture analysis, and model esophagus testing in accordance with the procedure set forth above.

Syneresis Analysis

| Batch # | Mass (g) Jun. 28, 2011 | Jun. 29, 2011 | Jun. 30, 2011 | Jul. 1, 2011 | Jul. 5, 2011 | Jul. 6, 2011 | % Loss | # Days | % Loss/Day |
|---|---|---|---|---|---|---|---|---|---|
| 62811-A | 3.47 | 3.41 | 3.33 | n/a | 3.09 | 3.02 | 12.97 | 8.00 | 1.62 |
| 62811-B | 3.34 | 3.28 | 3.20 | n/a | 2.99 | 2.87 | 14.07 | 8.00 | 1.76 |
| 62811-C | 3.50 | 3.45 | 3.35 | n/a | 3.11 | 3.03 | 13.43 | 8.00 | 1.68 |
| 62811-D | 3.69 | 3.38 | 3.24 | n/a | 2.85 | 2.70 | 26.83 | 8.00 | 3.35 |
| 62811-E | 3.91 | 3.69 | 3.56 | n/a | 3.20 | 3.09 | 20.97 | 8.00 | 2.62 |
| 62811-F | 3.31 | 3.21 | 3.07 | n/a | 2.73 | 2.63 | 20.54 | 8.00 | 2.57 |
| 62811-G | n/a | 3.67 | 3.49 | n/a | 3.16 | 3.02 | 17.71 | 7.00 | 2.53 |
| 63011-A | n/a | n/a | 3.06 | n/a | 2.82 | 2.74 | 10.46 | 6.00 | 1.74 |
| 63011-B | n/a | n/a | 3.59 | n/a | 3.37 | 3.27 | 8.91 | 6.00 | 1.49 |
| 7111-A | n/a | n/a | n/a | 3.79 | 3.57 | 3.50 | 7.65 | 5.00 | 1.53 |
| 7111-B | n/a | n/a | n/a | 2.95 | 2.60 | 2.51 | 14.92 | 5.00 | 2.98 |
| 7111-C | n/a | n/a | n/a | 3.39 | 3.04 | 2.96 | 12.68 | 5.00 | 2.54 |
| 7511-A | n/a | n/a | n/a | n/a | 2.74 | 2.67 | 2.55 | 1.00 | 2.55 |
| 7511-B | n/a | n/a | n/a | n/a | 2.56 | 2.48 | 3.13 | 1.00 | 3.13 |
| 7511-C | n/a | n/a | n/a | n/a | 3.33 | 3.25 | 2.40 | 1.00 | 2.40 |
| 7511-D | n/a | n/a | n/a | n/a | 3.48 | 3.40 | 2.30 | 1.00 | 2.30 |

Syneresis Analysis

| Batch # | Jun. 28, 2011 Mass (g) | Jun. 29, 2011 Mass (g) | Jun. 30, 2011 Mass (g) | Jul. 1, 2011 Mass (g) | Jul. 5, 2011 Mass (g) | Jul. 6, 2011 Mass (g) | % Loss | # Days | % Loss/Day |
|---|---|---|---|---|---|---|---|---|---|
| 7511-E | n/a | n/a | n/a | n/a | 3.37 | 3.30 | 2.08 | 1.00 | 2.08 |
| 7611-A | n/a | n/a | n/a | n/a | n/a | 2.44 | | | |
| 7611-B | n/a | n/a | n/a | n/a | n/a | 3.05 | | | |
| 7611-D | n/a | n/a | n/a | n/a | n/a | 3.25 | | | |
| 7611-E | n/a | n/a | n/a | n/a | n/a | 3.60 | | | |

Mass of Excipient (g)

| Batch # | Carrageenan | Xanthan Gum | Pullulan | Locust Bean Gum | KCl |
|---|---|---|---|---|---|
| 62811-F | 0.45 | 0.75 | 1.5 | 0.45 | 0.075 |
| 62811-A | 0.45 | 0.9 | 3 | 0.45 | 0.075 |
| 62811-B | 0.45 | 0.9 | 1.5 | 0.45 | 0.075 |
| 62811-C | 0.45 | 0.9 | 0 | 0.45 | 0.075 |
| 62811-D | 0.45 | 0.75 | 0 | 0.45 | 0.075 |
| 62811-E | 0.45 | 0.6 | 0 | 0.45 | 0.075 |
| 62811-G | 0.45 | 0.75 | 1.5 | 0.45 | 0.15 |
| 63011-A | 0.45 | 0.6 | 1.5 | 0.45 | 0.15 |
| 63011-B | 0.45 | 0.6 | 1.5 | 0.45 | 0.23 |
| 7111-A | 0.45 | 0.6 | 1.5 | 0.45 | 0.5 |
| 7111-B | 0.45 | 0.6 | 1.5 | 0.6 | 0.075 |
| 7111-C | 0.45 | 0.45 | 1.5 | 0.45 | 0.075 |
| 7511-A | 0.45 | 0.6 | 1.5 | 0.45 | 0.075 |
| 7511-B | 0.6 | 0.6 | 1.5 | 0.45 | 0.075 |
| 7511-C | 0.45 | 0.6 | 1.5 | 0.45 | 1 |
| 7511-D | 0.45 | 0.6 | 0.5 | 0.45 | 0.075 |
| 7511-E | 0.45 | 0.6 | 1.5* | 0.45 | 0.075 |
| 7611-A | 0.45 | 0.6 | 0.75* | 0.45 | 0.075 |
| 7611-B | 0.45 | 0.6 | 1.5 | 0.2 | 0.075 |
| 7611-C | 0.45 | 0 | 1.5 | 0.45 | 0.075 |
| 7611-D | 0.45 | 0.6 | 1.5 | 0.45 | 0 |
| 7611-E | 0.45 | 0.5 | 0.5 | 0.45 | 0.03 |

Measured at Rupture Point

| Batch # | Gel Strength (Pa) | Extensibility (%) | Rupture Point (Pa/%) | Notes |
|---|---|---|---|---|
| 62811-F | n/a | n/a | n/a | |
| 62811-A | 59721 | 80.755 | 739.53 | |
| 62811-B | 54884 | 82.253 | 667.26 | |
| 62811-C | 61561 | 79.57 | 773.67 | |
| 62811-D | 19996 | 67.561 | 295.97 | |
| 62811-E | 31600 | 67.592 | 467.51 | |
| 62811-G | 73906 | 77.685 | 951.35 | |
| 63011-A | 61496 | 79.576 | 772.8 | |
| 63011-B | 49246 | 78.028 | 631.13 | |
| 7111-A | 70694 | 81.448 | 867.96 | |
| 7111-B | 48603 | 80.228 | 605.81 | |
| 7111-C | 25425 | 75.709 | 335.83 | |
| 7511-A | 33563 | 80.448 | 417.2 | |
| 7511-B | 38273 | 76.92 | 497.57 | |
| 7511-C | 55606 | 77.759 | 715.11 | |
| 7511-D | 49113 | 79.932 | 614.43 | |
| 7511-E | 18146 | 65.856 | 275.54 | HPMC (K100M) |
| 7611-A | 43109 | 74.139 | 581.46 | HPMC (K100M) |
| 7611-B | 41932 | 81.981 | 511.48 | |
| 7611-C | 8761 | 73.27 | 119.57 | |
| 7611-D | 23271 | 74.355 | 312.97 | |
| 7611-E | 28805 | 75.936 | 379.33 | |

Example 6

The following Example includes details regarding various gels prepared in accordance with the above methods and also the results of texture analysis (e.g., gel strength, extensibility, and Young's modulus) gathered by the above-described methods.

| Batch # | Water (g) | Gellan (g) | Locust Bean Gum (g) | Xanthan Gum (g) | Sodium Citrate (g) |
|---|---|---|---|---|---|
| 52711-A | 150.0 | 0.70 | 0.45 | 0.45 | 0.0725 |
| 53111-A | 150.0 | 0.90 | 0.45 | 0.45 | 0.90 |
| 53111-B | 150.0 | 0.2250 | 0.45 | 0.45 | 0.0725 |
| 53111-C | 150.0 | 0.2250 | 0.45 | 0.90 | 0.0725 |
| 60111-A | 150.0 | 0.45 | 0.45 | 0.45 | 0.2175 |
| 60111-B | 150.0 | 0.90 | 0.2250 | 0.2250 | 0.45 |
| 60111-C | 150.0 | 0.45 | 0.2250 | 0.6750 | 0.45 |
| 60211-P | 150.0 | 0.50 | 0.30 | 0.70 | 0.50 |
| 60311-A | 150.0 | 0.30 | 0.30 | 0.75 | 0.45 |
| 60311-B | 150.0 | 0.15 | 0.45 | 0.75 | 0.45 |
| 60311-C | 150.0 | 0.30 | 0.30 | 0.75 | 0.90 |
| 60311-R | 150.0 | 0.50 | 0.50 | 0.50 | 0.50 |
| 60611-A | 150.0 | 0.30 | 0.5250 | 0.5250 | 0.90 |
| 60711-A | 150.0 | 0.30 | 0.5250 | 0.5250 | 0.45 |
| 60711-B | 150.0 | 0.30 | 0.30 | 0.30 | 0.45 |
| 60711-C | 150.0 | 0.30 | 0.45 | 0.30 | 0.45 |
| 60811-A | 150.0 | 0.30 | 0.45 | 0.20 | 0.45 |
| 60811-B | 150.0 | 0.30 | 0.60 | 0.20 | 0.45 |
| 60811-C | 150.0 | 0.30 | 0.60 | 0.30 | 0.45 |
| 60811-D | 150.0 | 0.20 | 0.60 | 0.30 | 0.45 |
| 60811-E | 150.0 | 0.40 | 0.60 | 0.30 | 0.45 |
| 61011-A | 150.0 | 0.20 | 0.60 | 0.30 | 0.45 |
| 61011-B | 150.0 | 0.20 | 0.60 | 0.30 | 0.45 |
| 61411-A | 150.0 | 0.30 | 0.60 | 0.30 | 0.30 |
| 61411-B | 150.0 | 0.30 | 0.60 | 0.30 | 0.60 |
| 61411-D | 150.0 | 0.30 | 0.60 | 0.20 | 0.60 |
| 61411-E | 150.0 | 0.20 | 0.60 | 0.30 | 0.60 |
| 61511-A | 150.0 | 0.20 | 0.60 | 0.30 | 0.60 |
| 61511-B | 150.0 | 0.20 | 0.60 | 0.30 | 0.60 |
| 61611-C | 150.0 | 0.30 | 0.60 | 0.30 | 0.45 |
| 61711-A | 150.0 | 0.30 | 0.60 | 0.30 | 0.40 |
| 61711-B | 150.0 | 0.30 | 0.60 | 0.30 | 0.30 |
| 61711-E | 150.0 | 0.30 | 0.60 | 0.40 | 0.60 |
| 62111-A | 147.0 | 0.0 | 0.30 | 0.75 | 1.50 |
| 62311-A | 147.0 | 0.3 | 0.30 | 0.75 | 1.50 |
| 62311-B | 147.0 | 0.3 | 0.30 | 0.75 | 1.00 |
| 62311-C | 147.0 | 0.3 | 0.30 | 0.75 | 0.50 |
| 62711-A | 150.0 | 0.3 | 0.60 | 0.60 | 1.00 |

| Batch # | Extensibility (%) | Strength (kPa) | Note | Young's Modulus (Pa/%) |
|---|---|---|---|---|
| 52711-A | 49.07 | 4.813 | | 11.52 |
| 53111-A | 62.46 | 5.12 | | 20.56 |
| 53111-B | 83.92 | 16.722 | | 16.50 |
| 53111-C | 96.60 | 54.765 | | 28.02 |
| 60111-A | 69.79 | 14.111 | | 24.60 |
| 60111-B | 52.93 | 0.909 | | 10.46 |

| Batch # | Extensibility (%) | Strength (kPa) | Note | Young's Modulus (Pa/%) |
|---|---|---|---|---|
| 60111-C | 67.34 | 10.917 | | 20.72 |
| 60211-P | 63.83 | 10.783 | | 22.67 |
| 60311-A | 69.17 | 17.911 | | 25.64 |
| 60311-B | 70.96 | 31.28 | | 29.33 |
| 60311-C | 70.09 | 20.979 | | 27.43 |
| 60311-R | 61.16 | 13.787 | | 28.82 |
| 60611-A | 73.17 | 28.637 | | 28.36 |
| 60711-A | 74.34 | 30.333 | | 33.58 |
| 60711-B | 69.35 | 8.918 | | 14.53 |
| 60711-C | 67.41 | 10.937 | | 17.64 |
| 60811-A | 69.53 | 8.344 | | 14.77 |
| 60811-B | 70.99 | 6.495 | | 12.78 |
| 60811-C | 69.02 | 13.313 | | 21.76 |
| 60811-D | 71.55 | 11.46 | | 16.65 |
| 60811-E | 67.35 | 7.257 | | 15.67 |
| 61011-A | 75.96 | 16.309 | 3.0 g Pullulan | 16.84 |
| 61011-B | 64.34 | 7.685 | 1.5 g Pullulan | 19.09 |
| 61411-A | 72.84 | 13.765 | | 19.46 |
| 61411-B | 71.91 | 14.027 | | 15.95 |
| 61411-D | 69.25 | 5.394 | | 10.47 |
| 61411-E | 71.78 | 15.368 | | 19.65 |
| 61511-A | 72.49 | 33.741 | 10% CaCO₃ | 42.03 |
| 61511-B | 75.21 | 26.597 | 25% CaCO₃ | 36.09 |
| 61611-C | 56.77 | 14.786 | NaCl | 54.85 |
| 61711-A | 59.77 | 14.548 | KCl | 34.96 |
| 61711-B | 67.37 | 9.047 | NaCl | 20.66 |
| 61711-E | 69.87 | 10.596 | | 19.09 |
| 62111-A | 88.18 | 55.292 | 0.30 g konjac | 23.66 |
| 62311-A | 66.29 | 19.879 | | 39.90 |
| 62311-B | 69.12 | 20.324 | | 30.47 |
| 62311-C | 64.88 | 9.533 | | 19.42 |
| 62711-A | 78.82 | 44.39 | | 41.26 |

| Batch # | Gelcarin 654B (g) | Xanthan Gum (g) | Pullulan (g) | Locust Bean Gum (g) | KCl (g) |
|---|---|---|---|---|---|
| 62811-A | 0.45 | 0.9 | 3 | 0.45 | 0.075 |
| 62811-B | 0.45 | 0.9 | 1.5 | 0.45 | 0.075 |
| 62811-C | 0.45 | 0.9 | 0 | 0.45 | 0.075 |
| 62811-D | 0.45 | 0.75 | 0 | 0.45 | 0.075 |
| 62811-E | 0.45 | 0.6 | 0 | 0.45 | 0.075 |
| 62811-G | 0.45 | 0.75 | 1.5 | 0.45 | 0.15 |
| 63011-A | 0.45 | 0.6 | 1.5 | 0.45 | 0.15 |
| 63011-B | 0.45 | 0.6 | 1.5 | 0.45 | 0.23 |
| 7111-A | 0.45 | 0.6 | 1.5 | 0.45 | 0.5 |
| 7111-B | 0.45 | 0.6 | 1.5 | 0.6 | 0.075 |
| 7111-C | 0.45 | 0.45 | 1.5 | 0.45 | 0.075 |
| 7511-A | 0.45 | 0.6 | 1.5 | 0.45 | 0.075 |
| 7511-B | 0.6 | 0.6 | 1.5 | 0.45 | 0.075 |
| 7511-C | 0.45 | 0.6 | 1.5 | 0.45 | 1 |
| 7511-D | 0.45 | 0.6 | 0.5 | 0.45 | 0.075 |
| 7511-E | 0.45 | 0.6 | 1.5 | 0.45 | 0.075 |
| 7611-A | 0.45 | 0.6 | 0.75 | 0.45 | 0.075 |
| 7611-B | 0.45 | 0.6 | 1.5 | 0.2 | 0.075 |
| 7611-C | 0.45 | 0 | 1.5 | 0.45 | 0.075 |
| 7611-D | 0.45 | 0.6 | 1.5 | 0.45 | 0 |
| 7611-E | 0.45 | 0.5 | 0.5 | 0.45 | 0.03 |
| 7711-A | 0.45 | 0.6 | 0.5 | 0.45 | 0 |
| 7711-B | 0.45 | 0.5 | 0.5 | 0 | 0.03 |
| 7711-C | 0.45 | 0.5 | 0.5 | 0.6 | 0.01 |
| 7711-D | 0 | 0.5 | 0.5 | 0.45 | 0.03 |

| Batch # | Gel Strength (Pa) | Extensibility (%) | Notes | Young's Modulus (Pa/%) |
|---|---|---|---|---|
| 62811-A | 32.186 | 72.462 | | 40.63 |
| 62811-B | 54884 | 82.253 | | 46.57 |
| 62811-C | 61561 | 79.57 | | 44.30 |
| 62811-D | 19996 | 67.561 | | 29.52 |
| 62811-E | 31600 | 67.592 | | 31.84 |
| 62811-G | 73906 | 77.685 | | 49.63 |
| 63011-A | 61496 | 79.576 | | 62.59 |
| 63011-B | 49246 | 78.028 | | 44.52 |
| 7111-A | 70694 | 81.448 | | 53.66 |
| 7111-B | 48603 | 80.228 | | 45.09 |
| 7111-C | 25425 | 75.709 | | 30.94 |
| 7511-A | 33563 | 80.448 | | 33.81 |
| 7511-B | 38273 | 76.92 | | 37.51 |
| 7511-C | 55606 | 77.759 | | 57.80 |
| 7511-D | 49113 | 79.932 | | 42.31 |
| 7511-E | 18146 | 65.856 | | 45.79 |
| 7611-A | 43109 | 74.139 | | 62.98 |
| 7611-B | 41932 | 81.981 | | 38.58 |
| 7611-C | 8761 | 73.27 | | 30.46 |
| 7611-D | 23271 | 74.355 | | 25.43 |
| 7611-E | 28805 | 75.936 | | 29.65 |
| 7711-A | 17449 | 73.973 | | 26.36 |
| 7711-B | 10201 | 73.459 | | 16.78 |
| 7711-C | 23356 | 76.625 | | 25.24 |
| 7711-D | 20924 | 93.911 | | 14.02 |

| Batch # | KCl (g) | CaCl2 (g) | Xanthan Gum (g) | Pullulan (g) | Kappa Carrageenan (g) | Iota Carrageenan (g) | Locust Bean Gum (g) |
|---|---|---|---|---|---|---|---|
| 72511-A | 0.3 | 0 | 0.6 | 0 | 0.375 | 0 | 0.45 |
| 72511-B | 0.3 | 0 | 0.6 | 0 | 0.45 | 0 | 0.45 |
| 72511-C | 0.2 | 0 | 0.6 | 0 | 0.45 | 0 | 0.45 |
| 72511-D | 0.2 | 0 | 0.6 | 0 | 0.4 | 0 | 0.6 |
| 72611-A | 0.2 | 0 | 0.6 | 0 | 0.5 | 0 | 0.5 |
| 72611-B | 0.2 | 0 | 0.6 | 0 | 0.6 | 0 | 0.4 |
| 72611-C | 0.2 | 0 | 0.2 | 0 | 0.5 | 0 | 0.5 |
| 72611-D | 0.2 | 0 | 0.6 | 0 | 0.2 | 0 | 0.3 |
| 72711-A | 0.2 | 0 | 0.6 | 0 | 0.25 | 0 | 0.25 |
| 72711-B | 0.2 | 0 | 0.6 | 0 | 0.3 | 0 | 0.2 |
| 72711-C | 0.2 | 0 | 0.6 | 0 | 0.25 | 0 | 0.25 |
| 72811-A | 0.2 | 0 | 0.6 | 1.5 | 0.3 | 0 | 0.2 |
| 72811-B | 0.2 | 0 | 0.6 | 1.5 | 0.2 | 0 | 0.3 |
| 72811-C | 0 | 0 | 0.6 | 0 | 0 | 0.25 | 0.25 |
| 72911-A | 0 | 0.3 | 0.6 | 0 | 0 | 0.25 | 0.25 |
| 72911-B | 0 | 0.3 | 0.6 | 0 | 0 | 0.3 | 0.3 |

-continued

| Batch # | KCl (g) | CaCl2 (g) | Xanthan Gum (g) | Pullulan (g) | Kappa Carrageenan (g) | Iota Carrageenan (g) | Locust Bean Gum (g) |
|---|---|---|---|---|---|---|---|
| 72911-C | 0 | 0.3 | 0.6 | 0 | 0 | 0.4 | 0.4 |
| 8211-A | 0 | 0.3 | 0.6 | 3 | 0 | 0.4 | 0.4 |
| 8311-A | 0 | 0.3 | 0.6 | 2 | 0 | 0.4 | 0.4 |
| 8311-B | 0.3 | 0 | 0.6 | 2 | 0.4 | 0 | 0.4 |

| Batch # | Gel Strength (kPa) | Extensibility (%) | Young's Modulus (Pa/%) |
|---|---|---|---|
| 72511-A | 87.492 | 75.184 | 49.48 |
| 72511-B | 73.501 | 65.544 | 94.04 |
| 72511-C | 73.797 | 74.549 | 72.19 |
| 72511-D | 98.181 | 78.216 | 83.22 |
| 72611-A | 110.199 | 76.278 | 65.18 |
| 72611-B | 87.776 | 72.863 | 95.99 |
| 72611-C | 57.453 | 67.354 | 98.24 |
| 72611-D | 67.334 | 81.169 | 33.86 |
| 72711-A | 46.319 | 74.075 | 32.44 |
| 72711-B | 30.24 | 61.555 | 25.71 |
| 72711-C | 68.069 | 78.724 | 48.56 |
| 72811-A | 63.237 | 80.203 | 41.12 |
| 72811-B | 66.378 | 81.832 | 40.98 |
| 72811-C | 24.656 | 71.431 | 23.05 |
| 72911-A | 11.284 | 63.034 | 21.91 |
| 72911-B | 21.173 | 68.545 | 21.99 |
| 72911-C | 24.504 | 69.257 | 16.94 |
| 8211-A | 23.027 | 77.895 | 22.31 |
| 8311-A | 14.556 | 65.758 | 17.44 |
| 8311-B | 55.989 | 69.854 | 46.89 |

Example 7

The following describes preparation of a sustained release acetaminophen gel dosage form (650 mg XR).

135.0 g deionized (DI) $H_2O$, 0.30 g $CaCl_2$, 0.10 g sodium benzoate, 0.06 g methyl paraben, 0.25 g xylitol and 0.05 g sucralose were weighed out and placed in a 250 ml beaker. The mixture was stirred using a magnetic stir bar until all components were dissolved in the water.

The stir bar was removed and, using an overhead mixer equipped with a 1.5" 3 blade impeller, the solution was stirred at 250 rpm. The beaker was then covered and the solution was heated to 85-90° C.

0.40 g locust bean gum, 0.40 g iota-carrageenan, 0.60 g xanthan gum and 0.30 g gum tragacanth were weighed out and placed in a 50 ml beaker. 2 ml glycerol were added and the resulting mixture was stirred with a stirring rod until all of the gums/gelling agents were dispersed throughout the glycerol.

The mixing rate of the aqueous solution was then increased to 350 rpm. The glycerol/gelling agent dispersion was then added to the aqueous solution and this mixture was stirred for 20 minutes.

19.5 g acetaminophen (13%) was then weighted out and added to the solution, which was then stirred for another 20 minutes.

15.0 g DI $H_2O$, 0.15 ml Tween 80 and 15.0 g $CaCO_3$ were then weighed out, placed in a 50 ml beaker, and stirred with a stir rod. The mixing rate of the overhead mixer was then increased to 400 rpm, $CaCO_3$ was added to the dispersion, and the dispersion was stirred for another 20 minutes.

5.0 g of the resulting dispersion/gel mixture was then placed in a mold and allowed to cool to room temperature.

Example 8

The following example describes a method for preparation of fish oil (25%) gel.

In a 250 ml beaker weigh out 150.0 g DI $H_2O$, 0.30 g $CaCl_2$, 0.10 g sodium benzoate, 0.06 g methyl paraben, 0.25 g xylitol and 0.05 g sucralose. Stir the mixture using a magnetic stir bar until all components have been dissolved in the water.

Remove the stir bar; using an overhead mixer equipped with a 1.5" 3 blade impeller, stir the solution at 250 rpm. Cover the beaker and heat the solution to 85-90° C.

In a 50 ml beaker weigh out 0.40 g locust bean gum, 0.40 g iota-carrageenan, 0.60 g xanthan gum and 0.30 g gum tragacanth. Add 2 ml glycerol and mix with a stir rod until all of the gums/gelling agents are dispersed throughout the glycerol.

Increase the mixing rate of the aqueous solution to 350 rpm. Add the glycerol/gelling agent dispersion to the aqueous solution and stir for 20 minutes.

Add 1.5 g (1% of aqueous) Tween 80 to the gel solution.

In a 100 ml beaker weigh out 0.375 g Span 80 (1% of oil) and 37.5 g fish oil. Stir with a stir rod then add the fish oil mixture to the gel solution. Stir the resulting mixture for 20 minutes.

Add any color/flavor desired.

Pour desired dose size and shape and allow to cool.

Example 9

The following example describes a method for preparing a diversion resistant pseudoephedrine HCl (60 mg) gel.

In a 250 ml beaker weigh out 150.0 g DI $H_2O$, 0.30 g $CaCl_2$, 0.10 g sodium benzoate, 0.06 g methyl paraben, 0.25 g xylitol and 0.05 g sucralose. Stir mixture using a magnetic stir bar until all components have dissolved in the water.

Remove the stir bar; using an overhead mixer equipped with a 1.5" 3 blade impeller, stir the solution at 250 rpm. Cover the beaker and heat the solution to 85-90° C.

In a 50 ml beaker weigh out 0.40 g locust bean gum, 0.40 g iota-carrageenan, 0.60 g xanthan gum and 0.30 g gum tragacanth. Add 2 ml glycerol and mix with a stir rod until all of the gums/gelling agents are dispersed.

Increase the mixing rate of the overhead mixer to 350 rpm. Add the glycerol/gelling agent dispersion to the aqueous solution and stir for 20 minutes.

Add 1.5 ml (1% of aqueous) Tween 80 and 3.0 g pseudoephedrine HCl. Stir for 20 minutes.

Add any color/flavor desired.

Pour out 3.0 g doses in the desired shape/size and allow to cool.

Example 10

This Example provides dissolution data for acetaminophen-containing (APAP) gels prepared in accordance with the present invention, in particular, Example 7 set forth above.

Dissolution testing was conducted generally in accordance with the method described in Example 1, in particular under the following conditions:

Blank: pH 1.2 HCl

Bath: 900 ml, pH 1.2 HCl at 37.5° C.

Mixing Type: paddle

Mixing Rate: 50 revolutions per minute (rpm)

Detector: UV-Vis, 250 nanometers (nm).

Figure 6A:
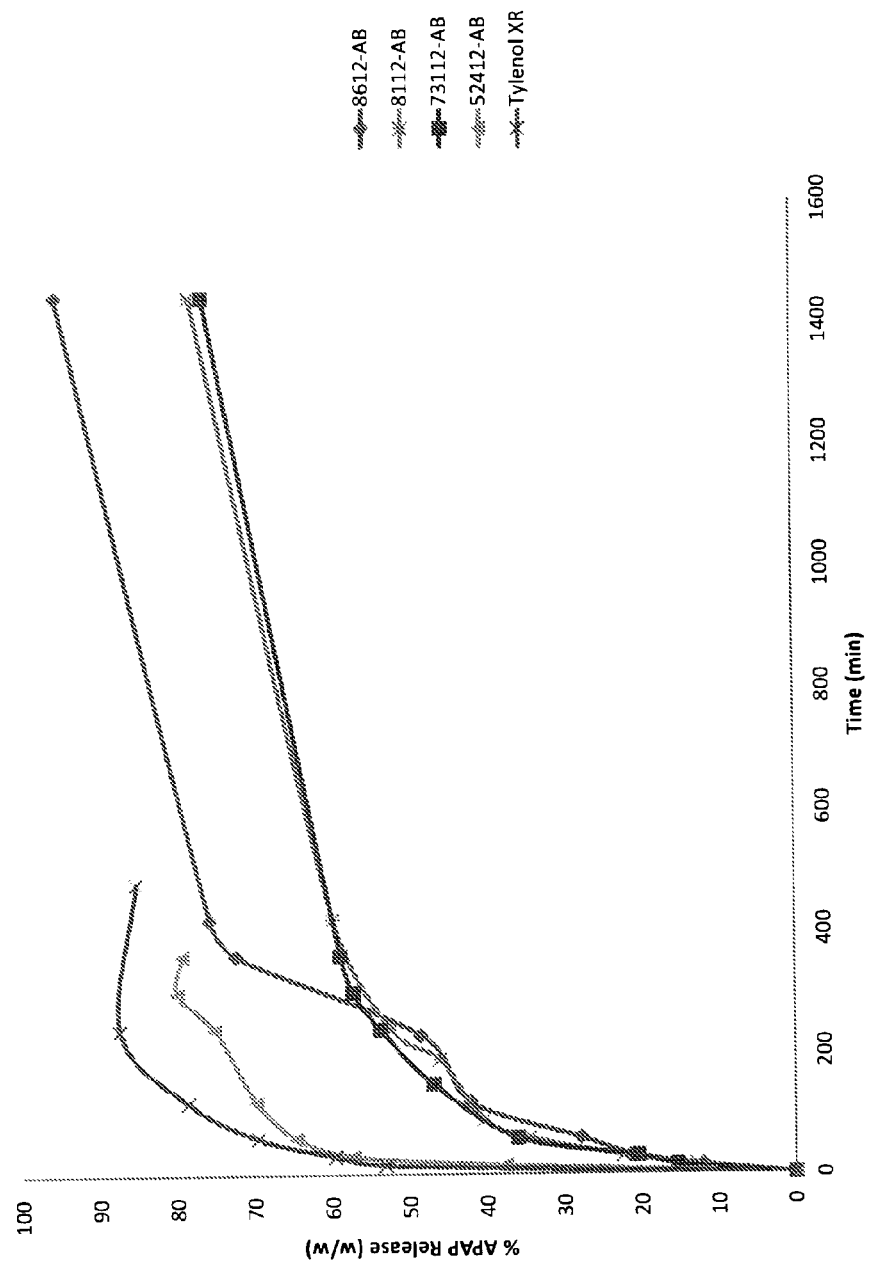
FIGS. 6A and 6B provide the results of acetaminophen dissolution testing described in Example 10.
Figure 6B:
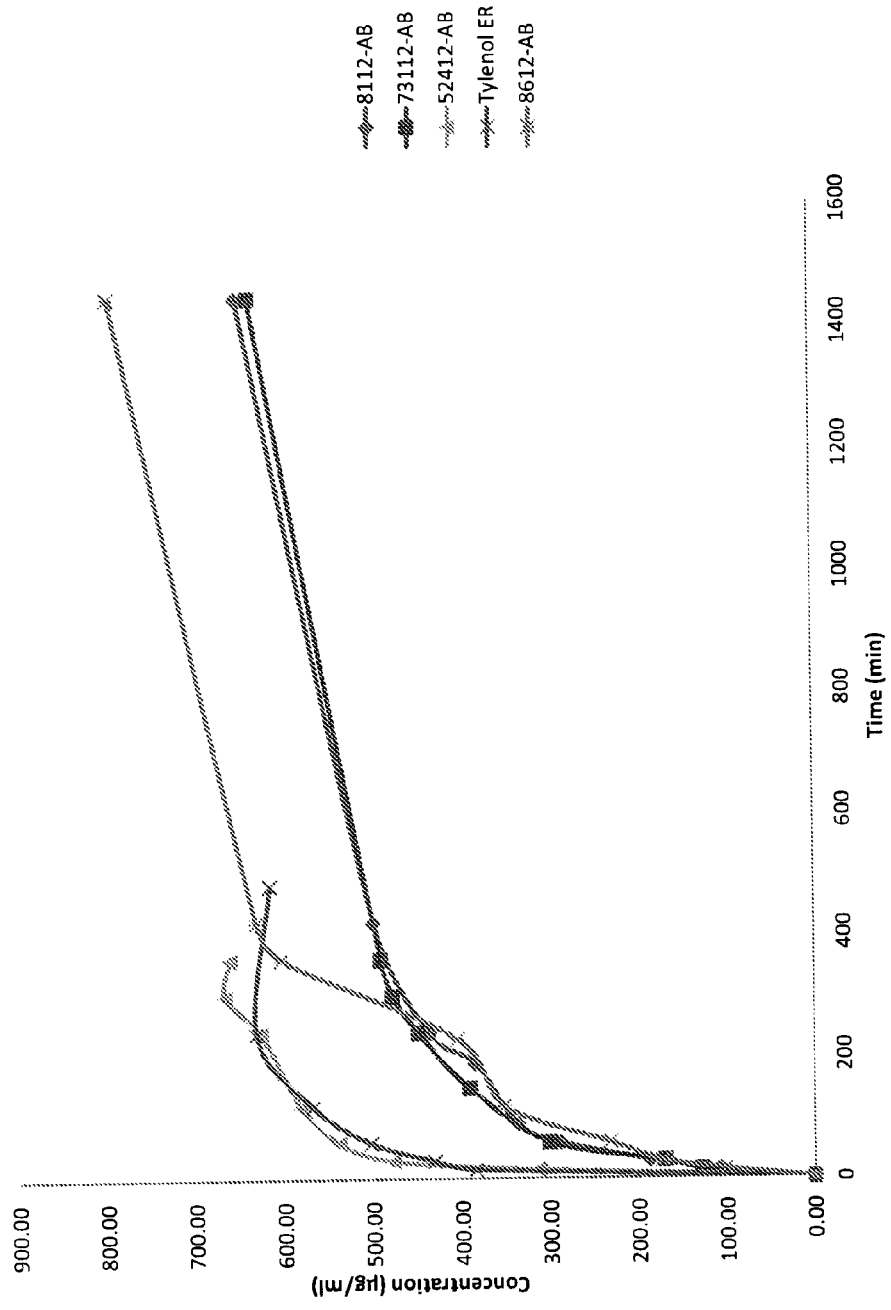

The dissolution profiles are set forth in FIGS. 6A and 6B. For comparison purposes, dissolution profiles were also generated for TYLENOL Arthritis Pain extended release (ER) Bi-layer Tablet (650 mg), as shown in FIGS. 6A and 6B. Based on these dissolution profiles, it is currently believed that when administered to a subject these gels will provide initial loadings of acetaminophen and also extended release of acetaminophen. In particular, it is currently believed that these gels will provide release of the active acetaminophen for at least 8 hours and also provide pain relief for a period of 12 hours based on the serum blood levels expected to be provided by the gels.

The data underlying the dissolution profiles are set forth in the following Tables:

| 8112-AB | | |
|---|---|---|
| Time (min) | % Release | Concentration (µg/ml) |
| 0 | 0.00 | 0.00 |
| 15 | 13.01 | 108.44 |
| 30 | 22.43 | 186.93 |
| 60 | 34.48 | 287.36 |
| 90 | 40.42 | 336.83 |
| 190 | 46.14 | 384.52 |
| 240 | 52.35 | 436.24 |
| 420 | 59.80 | 498.30 |
| 1440 | 77.80 | 648.32 |

| 73112-AB | | |
|---|---|---|
| Time (min) | % Release | Concentration (µg/ml) |
| 0 | 0.00 | 0.00 |
| 15 | 15.42 | 128.52 |
| 30 | 20.45 | 170.45 |
| 60 | 36.10 | 300.82 |
| 150 | 46.93 | 391.05 |
| 240 | 53.79 | 448.28 |
| 300 | 57.26 | 477.20 |
| 360 | 58.87 | 490.62 |
| 1440 | 76.14 | 634.51 |

| 52412-AB | | |
|---|---|---|
| Time (min) | % Release | Concentration (µg/ml) |
| 0 | 0.00 | 0.00 |
| 15 | 37.60 | 313.32 |
| 30 | 57.33 | 477.79 |
| 60 | 64.62 | 538.49 |
| 120 | 69.75 | 581.21 |
| 240 | 75.12 | 625.99 |
| 300 | 79.98 | 666.48 |
| 360 | 79.30 | 660.85 |

| TYLENOL ER | | |
|---|---|---|
| Time (min) | % Release | Concentration (µg/ml) |
| 0 | 0.00 | 0.0000 |
| 15 | 53.16 | 383.9530 |
| 30 | 59.64 | 430.7554 |
| 60 | 69.60 | 502.6957 |
| 120 | 78.63 | 567.8726 |
| 240 | 87.39 | 631.1216 |
| 480 | 85.13 | 614.7963 |

| 8612-AB | | |
|---|---|---|
| Time (min) | % Release | Concentration (µg/ml) |
| 0 | 0 | 0 |
| 15 | 12.15 | 101.21 |
| 30 | 20.82 | 173.53 |
| 60 | 27.88 | 232.36 |
| 120 | 42.22 | 351.83 |
| 230 | 48.52 | 404.34 |
| 360 | 72.33 | 602.76 |
| 420 | 75.66 | 630.53 |
| 1440 | 95.15 | 792.88 |

Example 11

This Example describes preparation of a bi-layer gel of the present invention including acetaminophen as the active ingredient, an instant release layer, and an extended release layer.

Instant Release (IR) Layer:

In a 250 ml beaker, the following were placed: 150 g of deionized water (DI H2O), 0.30 g CaCl2, 0.06 g methyl paraben, 0.03 g propyl paraben, and 0.10 g sodium benzoate. The components were mixed using an overhead mixer with a 1.5" 3 blade impeller at 250 revolutions per minute (rpm). Once mixing was completed, the beaker was covered and heated to approximately 85-90° C.

In a separate beaker, the following ingredients were dispersed into 2.5 ml glycerol: 0.50 g iota-carrageenan, 0.50 g locust bean gum, 0.30 g tragacanth and 0.80 g xanthan gum. After heating, this gel/gum dispersion was added to the aqueous solution prepared above. The combined mixture was mixed at approximately 350 rpm until all gums are dispersed.

Once dispersed, acetaminophen (38.7 g) was added and the gel was allowed to cool to approximately 60-65° C. and stored until needed preparation of the bi-layer gel.

Extended Release (ER) Layer:

The following ingredients were weighed out and placed in a 250 ml beaker: 135 g DI H2O, 0.30 g CaCl2, 0.06 g methyl paraben, 0.03 g propyl paraben and 0.10 g sodium benzoate. These ingredients were mixed using an overhead mixer with a 1.5" 3 blade impeller operated at 250 rpm. The beaker was then covered and heated to approximately 85-90° C.

In a separate beaker the following ingredients were dispersed into 2.5 ml glycerol: 0.50 g iota-carrageenan, 0.50 g locust bean gum, 0.30 g tragacanth and 0.80 g xanthan gum. Once heated, the gum dispersion was added to the aqueous solution. The mixing rate was then increased to approximately 350 rpm and the ingredients were mixed until all of the gums were dispersed. Once dispersed, the total gel weight was determined.

In another clean beaker, the following ingredients were added: 15 g DI H2O, 0.10 ml Tween 80 and a suitable amount of CaCO3 (e.g., from 15-20% w/w). A stir rod was used to mix into a paste then this paste was added to the gel and the resulting mixture was mixed for approximately 20 minutes. The total gel weight was then determined once again.

In another clean beaker, acetaminophen (18.6 g) was placed along with compritol (0.75 g, 4% of the weight of acetaminophen). The beaker was then placed in a water bath at approximately 80° C. and mixed with a stir rod. Once the compritol was melted, the beaker was removed from the water bath and mixing was continued using a stir rod until the mixture cooled to room temperature.

The gel solution was then allowed to cool to approximately 60° C. and the coated active ingredient was mixed until dispersed (e.g., for approximately 20 minutes).

The bi-layer gel was prepared by casting 1 g of the IR layer into a suitable mold, followed by casting of 5 g of the ER layer into the mold after casting of the IR layer.

Example 12

Method of Preparation of Omega-3 Gel

Compositions of the gel prepared in accordance with the following method, including the amounts/proportions of the individual components, are described in Example 13.

The following ingredients were placed in a 250 ml beaker to form an aqueous fraction: DI H$_2$O, whey protein, malic acid, and ethylenediaminetetraacetic acid (EDTA), CaCl$_2$, Phospholipon, ascorbic acid, sweeteners (xylitol, sucralose), sodium benzoate, methyl paraben, and potassium sorbate.

These components were mixed at room temperature for approximately, but not less than 20 minutes until dispersed.

An oil-based fraction was formed by mixing the following ingredients in a vacuum flask under a nitrogen blanket: oil soluble flavors, lemon oil, and rosemary oil, tocopherol, ascorbyl palmitate, and fish oil.

These components were mixed at room temperature under a nitrogen blanket until dispersed for approximately 5 minutes.

The aqueous fraction was combined with the oil fraction and the mixed fractions were mixed with a high shear homogenizer. Once the aqueous and oil fractions are combined, the resulting emulsion was maintained under a nitrogen blanket.

The emulsion was then transferred to a 600 ml beaker (while still under a nitrogen blanket), covered, and stirred using a stir bar.

Sodium hydroxide (50 wt %) was added to the emulsion to adjust its pH to approximately 3.9-4.0. The emulsion was then heated to approximately 70-75° C., after which time the stir bar was removed and the mixture was mixed using an overhead mixer at approximately 250 rpm.

In a separate beaker, the following components were mixed: glycerol, locust bean gum, iota-carraageenan, xanthan gum, and gum tragacanth. These components were mixed using a stir rod until dispersed, forming a paste, which was filled into a syringe and combined with the emulsion prepared as described above. While combining the paste with the emulsion, as viscosity was increased, the mixing rate was increased to 650 rpm until mixing was complete. Water soluble flavor and color (complimentary to the flavor used) were then added, followed by continued mixing at 650 rpm for approximately 5 minutes. Desired volumes were then placed into blister molds and sealed under nitrogen.

Example 13

Omega-3 Gels

The following table details components of an omega-3 gel composition of the present invention.

| Purpose | Ingredients | Mass Per Batch (g) | Concentration (% w/w) | Mass per Dose (mg) |
|---|---|---|---|---|
| | Water | 150.000 | 60.29 | 3014.70 |
| Complexing Agent | CaCl2 | 0.300 | 0.12 | 6.03 |
| Emulsion Stabilizer | Whey Protein | 3.740 | 1.50 | 75.17 |
| Emulsifier | Phospholipon | 1.680 | 0.68 | 33.76 |
| Preservatives | Potassium Sorbate | 0.180 | 0.07 | 3.62 |
| | Methyl Paraben | 0.050 | 0.02 | 1.00 |
| | Sodium Benzoate | 0.050 | 0.02 | 1.00 |
| Chelator | EDTA | 0.002 | 0.001 | 0.04 |
| Anti-oxidant | Ascorbyl Palmitate | 0.009 | 0.004 | 0.18 |
| Anti-oxidant | Tocopherols | 0.010 | 0.004 | 0.20 |
| Sweetener | Xylitol | 2.0 | 0.80 | 40.20 |
| Sweetener | Sucralose | 0.3 | 0.12 | 6.03 |
| pH modifier taste modifier | Malic Acid | 0.5 | 0.20 | 10.05 |
| pH modifier/ oxygen scavenger | Ascorbic Acid | 0.5 | 0.20 | 10.05 |
| Flavor | Water Soluble Flavor | 3.0 | 1.21 | 60.29 |
| processing agent | Glycerol | 3.0 | 1.21 | 60.29 |
| Gelling Agents | Iota Carrageenan | 0.9 | 0.35 | 17.69 |
| | Locust Bean Gum | 0.9 | 0.35 | 17.69 |
| | Xanthan Gum | 1.1 | 0.44 | 22.11 |
| | Tragacanth | 0.6 | 0.22 | 11.05 |
| Flavor/Taste Masker | Oil Soluble Flavor | 4 | 1.61 | 80.39 |
| Taste masker | Lemon Oil | 1 | 0.40 | 20.10 |
| Taste masker | Rosemary Oil | 0.15 | 0.06 | 3.01 |
| Active | Fish Oil | 74.6 | 29.99 | 1499.31 |
| pH modifier | 50% NaOH | 0.3 | 0.12 | 6.03 |
| | Total | 248.781 | 100.0000 | 5000.00 |

Example 14

This Example details results of texture analysis (e.g., gel strength, extensibility, and Young's modulus) as described in Example 3 above and syneresis testing for omega-3-containing gels described in Example 13.

| | | | Texture Analysis | | |
|---|---|---|---|---|---|
| Sample | Stress (Pa) | Strain (%) | Young Modulus (Pa/%) | Pa/cm2 | At rupture point Pa/% |
| 1 | 30575 | 67.51 | 40.099 | 6.0340234 | 452.89589 |
| 2 | 26317 | 71.911 | 37.157 | 5.193701 | 365.9663 |
| 3 | 28709 | 71.663 | 47.915 | 5.665765 | 400.6112 |
| Average | 28533.667 | 70.36133333 | 41.72366667 | 5.631163 | 405.5305 |

| | | Syneresis | | |
|---|---|---|---|---|
| Date | Mass (g) | % Water Loss | #Days | % Loss/Day |
| Day 1 | 4.15 | 0.96 | 4.00 | 0.24 |
| Day 5 | 4.11 | | | |
| Difference | 0.04 | | | |

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

What is claimed is:

1. An aqueous deformable gel emulsion composition, the emulsion comprising a lipophilic phase dispersed within a gelled aqueous phase, and an emulsifier, wherein the lipophilic phase comprises a lipophilic active ingredient, and the gelled aqueous phase comprises water and one or more gelling agents, wherein:
   water constitutes from about 30 wt % to about 60 wt % of the composition;
   the gelling agents consist essentially of xanthan gum, locust bean gum, iota-carrageenan, and gum tragacanth;
   each of xanthan gum, locust bean gum, iota-carrageenan, and gum tragacanth constitutes from about 0.5 to about 1.5 wt % of the composition; and
   the composition further comprises a source of calcium ions selected from the group consisting of calcium acetate, calcium chloride, calcium carbonate, calcium ascorbate, and combinations thereof in a proportion of from about 0.1 to about 1 wt %.

2. The composition of claim 1 wherein the weight ratio of the lipophilic phase to the aqueous phase is from about 0.25:1 to about 0.8:1.

3. The composition of claim 1 wherein the emulsifier is a non-ionic emulsifier selected from the group consisting of whey protein, lecithin, sorbitan mono-oleate, polyoxyethylene sorbitan mono-oleate, and combinations thereof.

4. The composition of claim 1 wherein the gel (i) has a Young's modulus (Pa/% strain) of from about 10 to about 95; and/or (ii) the gel has a Young's modulus (Pa/% strain) per unit composition surface area of from about 0.25 Pa/cm$^2$ to about 10 Pa/cm$^2$.

5. The composition of claim 1 wherein the gel strength per unit composition surface area is from about 0.1 to about 1.75 kPa/cm$^2$.

6. The composition of claim 1 wherein the gel has an extensibility of from about 50% to about 90%.

7. The composition of claim 1 wherein syneresis of the composition during storage under ambient conditions for 90 days is less than about 10%.

8. The composition of claim 1 wherein syneresis of the composition during storage under ambient conditions for 90 days is less than about 7%.

9. The composition of claim 1 wherein the composition exhibits a gel strength at its rupture point of at least 1 kPa.

10. The composition of claim 1 wherein the composition exhibits a gel strength at its rupture point of at least 10 kPa.

11. The composition of claim 1 wherein the composition exhibits a gel strength at its rupture point of from about 20 kPa to about 50 kPa.

12. The composition of claim 1 wherein the composition exhibits a melting point of at least 40° C.

13. The composition of claim 1 wherein the composition exhibits a gel strength at its rupture point of about 1 kPa and a melting point of at least 40° C.

14. The composition of claim 1 wherein the composition has a shape selected from the group consisting of cylindrical, spherical, oval, rectangular, and square.

15. The composition of claim 1 wherein water constitutes from about 30 wt % to about 50 wt % of the composition.

16. The composition of claim 1 wherein the source of calcium ions is calcium chloride.

17. The composition of claim 16 wherein calcium chloride is present in a proportion of from about 0.2 to about 0.6 wt %.

18. An aqueous deformable gel emulsion composition, the emulsion comprising a lipophilic phase dispersed within a gelled aqueous phase, and an emulsifier, wherein the lipophilic phase comprises a lipophilic active ingredient, and the gelled aqueous phase comprises water and one or more gelling agents, wherein:
   water constitutes from about 30 wt % to about 60 wt % of the composition;
   the gelling agents consist essentially of xanthan gum, locust bean gum, iota-carrageenan, and gum tragacanth, each of xanthan gum, locust bean gum, iota-carrageenan, and gum tragacanth constituting from about 0.5 to about 1.5 wt % of the composition;

the composition further comprises calcium chloride in a proportion of from about 0.1 to about 1 wt %; and the composition exhibits a gel strength at its rupture point of at least 1 kPa and a melting point of at least 40° C.

* * * * *